(12) United States Patent
Kreutzer et al.

(10) Patent No.: US 8,114,981 B2
(45) Date of Patent: *Feb. 14, 2012

(54) METHOD AND MEDICAMENT FOR INHIBITING THE EXPRESSION OF A GIVEN GENE

(75) Inventors: Roland Kreutzer, Weidenberg (DE); Stefan Limmer, Kulmbach (DE)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 790 days.

This patent is subject to a terminal disclaimer.

(21) Appl. No.: 11/982,441

(22) Filed: Oct. 31, 2007

(65) Prior Publication Data

US 2008/0171861 A1     Jul. 17, 2008

Related U.S. Application Data

(60) Continuation of application No. 10/612,179, filed on Jul. 2, 2003, which is a division of application No. 09/889,802, filed as application No. PCT/DE00/00244 on Jan. 29, 2000, now abandoned.

(30) Foreign Application Priority Data

Jan. 30, 1999 (DE) .................... 199 03 713
Nov. 24, 1999 (DE) .................... 199 56 568

(51) Int. Cl.
*C07H 21/04* (2006.01)
*A61K 31/70* (2006.01)

(52) U.S. Cl. .......................... 536/24.5; 514/44

(58) Field of Classification Search .............. None
See application file for complete search history.

(56) References Cited

U.S. PATENT DOCUMENTS

| | | | |
|---|---|---|---|
| 4,868,116 A | 9/1989 | Morgan et al. | |
| 4,980,286 A | 12/1990 | Morgan et al. | |
| 4,987,071 A | 1/1991 | Cech et al. | |
| 5,107,065 A | 4/1992 | Shewmaker et al. | |
| 5,112,734 A | 5/1992 | Kramer et al. | |
| 5,190,931 A | 3/1993 | Inouye | |
| 5,208,149 A | 5/1993 | Inouye | |
| 5,212,295 A | 5/1993 | Cook | |
| 5,225,347 A | 7/1993 | Goldberg et al. | |
| 5,246,921 A | 9/1993 | Reddy et al. | |
| 5,254,678 A | 10/1993 | Haseloff et al. | |
| 5,328,470 A | 7/1994 | Nabel et al. | |
| 5,496,698 A | 3/1996 | Draper et al. | |
| 5,525,468 A | 6/1996 | McSwiggen | |
| 5,573,046 A | 11/1996 | Kmiec et al. | |
| 5,574,142 A | 11/1996 | Meyer, Jr. et al. | |
| 5,587,361 A | 12/1996 | Cook et al. | |
| 5,616,459 A | 4/1997 | Kramer et al. | |
| 5,624,803 A | 4/1997 | Noonberg | |
| 5,635,385 A | 6/1997 | Leopold et al. | |
| 5,639,655 A | 6/1997 | Thompson et al. | |
| 5,674,683 A | 10/1997 | Kool | |
| 5,703,054 A | 12/1997 | Bennett et al. | |
| 5,712,257 A | 1/1998 | Carter | |
| 5,719,271 A | 2/1998 | Cook et al. | |
| 5,731,181 A | 3/1998 | Kmiec | |
| 5,739,271 A * | 4/1998 | Sridhar et al. ............... 530/300 |
| 5,789,230 A | 8/1998 | Cotton et al. | |
| 5,801,154 A | 9/1998 | Baracchini et al. | |
| 5,811,275 A | 9/1998 | Wong-Staal et al. | |
| 5,811,300 A | 9/1998 | Sullivan et al. | |
| 5,814,500 A | 9/1998 | Dietz | |
| 5,824,519 A | 10/1998 | Norris et al. | |
| 5,837,510 A | 11/1998 | Goldsmith et al. | |
| 5,854,067 A | 12/1998 | Newgard et al. | |
| 5,864,028 A | 1/1999 | Sioud | |
| 5,866,701 A | 2/1999 | Hampel et al. | |
| 5,891,717 A | 4/1999 | Newgard et al. | |
| 5,898,031 A | 4/1999 | Crooke | |
| 5,908,779 A | 6/1999 | Carmichael et al. | |
| 5,939,262 A | 8/1999 | Pasloske et al. | |
| 5,968,737 A | 10/1999 | Ali-Osman et al. | |
| 5,985,620 A | 11/1999 | Sioud | |
| 5,998,203 A | 12/1999 | Matulic-Adamic et al. | |
| 6,025,167 A | 2/2000 | Cech et al. | |
| 6,054,299 A | 4/2000 | Conrad | |
| 6,057,156 A | 5/2000 | Akhtar et al. | |
| 6,071,890 A | 6/2000 | Scheule et al. | |
| 6,077,705 A | 6/2000 | Duane et al. | |
| 6,080,851 A | 6/2000 | Pachuk et al. | |
| 6,087,164 A | 7/2000 | Hochberg et al. | |
| 6,087,172 A | 7/2000 | Veerapaneni et al. | |
| 6,099,823 A | 8/2000 | Falb | |
| 6,100,087 A | 8/2000 | Rossi et al. | |
| 6,100,444 A | 8/2000 | Frelinger et al. | |
| 6,107,094 A | 8/2000 | Crooke | |
| 6,127,533 A | 10/2000 | Cook et al. | |
| 6,166,197 A | 12/2000 | Cook et al. | |
| 6,183,959 B1 | 2/2001 | Thompson | |
| 6,225,291 B1 | 5/2001 | Lewin et al. | |
| 6,245,560 B1 | 6/2001 | Lisziewicz | |
| 6,245,748 B1 | 6/2001 | Wellstein et al. | |
| 6,255,071 B1 | 7/2001 | Beach et al. | |
| 6,271,358 B1 | 8/2001 | Manoharan et al. | |
| 6,346,398 B1 | 2/2002 | Pavco et al. | |
| 6,355,415 B1 | 3/2002 | Wagner et al. | |
| 6,423,489 B1 | 7/2002 | Anderson et al. | |
| 6,482,803 B1 | 11/2002 | Ruth et al. | |
| 6,486,299 B1 | 11/2002 | Skimkets | |
| 6,506,559 B1 | 1/2003 | Fire et al. | |

(Continued)

FOREIGN PATENT DOCUMENTS

AU         717543     12/1997

(Continued)

OTHER PUBLICATIONS

Gao et al. Nucleic Acids Research 1995, vol. 23, pp. 285-292.*

(Continued)

*Primary Examiner* — Tracy Vivlemore
(74) *Attorney, Agent, or Firm* — Fenwick & West LLP

(57) ABSTRACT

The invention relates to an isolated RNA that mediates RNA interference of an mRNA to which it corresponds and a method of mediating RNA interference of mRNA of a gene in a cell or organism using the isolated RNA.

22 Claims, 5 Drawing Sheets

U.S. PATENT DOCUMENTS

Figure 1:
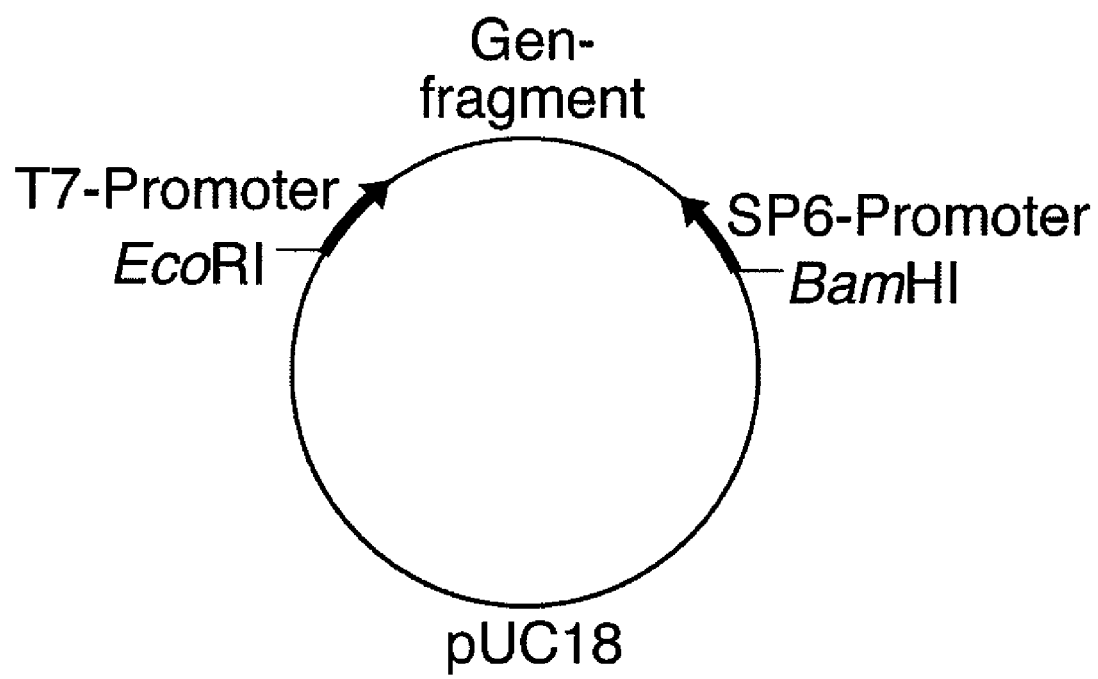

| | | |
|---|---|---|
| 6,573,046 B1 | 6/2003 | Kmiec et al. |
| 2002/0086356 A1 | 7/2002 | Tuschl et al. |
| 2002/0114784 A1 | 8/2002 | Li et al. |
| 2002/0123034 A1 | 9/2002 | Canaani et al. |
| 2002/0132346 A1 | 9/2002 | Cibelli et al. |
| 2002/0162126 A1 | 10/2002 | Beach et al. |
| 2002/0173478 A1 | 11/2002 | Gewirtz |
| 2003/0027783 A1 | 2/2003 | Zernicka-Goetz et al. |
| 2003/0108923 A1 | 6/2003 | Tuschl et al. |
| 2003/0125281 A1 | 7/2003 | Lewis et al. |
| 2003/0134808 A1 | 7/2003 | Wengel |
| 2003/0143732 A1 | 7/2003 | Fosnaugh et al. |
| 2003/0148341 A1 | 8/2003 | Sin et al. |
| 2003/0157030 A1 | 8/2003 | Davis et al. |
| 2003/0176671 A1 | 9/2003 | Reed et al. |
| 2003/0180756 A1 | 9/2003 | Shi et al. |
| 2003/0190635 A1 | 10/2003 | McSwiggen |
| 2003/0198627 A1 | 10/2003 | Arts et al. |
| 2004/0001811 A1 | 1/2004 | Kreutzer et al. |
| 2004/0053875 A1 | 3/2004 | Kreutzer et al. |
| 2004/0072779 A1 | 4/2004 | Kreutzer et al. |
| 2004/0102408 A1 | 5/2004 | Kreutzer et al. |
| 2006/0258608 A1 | 11/2006 | Meyers |
| 2008/0166800 A1 | 7/2008 | Kreutzer et al. |
| 2008/0171862 A1 | 7/2008 | Kreutzer et al. |
| 2008/0182981 A1 | 7/2008 | Kreutzer et al. |
| 2008/0233651 A1 | 9/2008 | Kreutzer et al. |
| 2008/0261303 A1 | 10/2008 | Kreutzer et al. |

FOREIGN PATENT DOCUMENTS

| | | |
|---|---|---|
| AU | 778474 | 8/2000 |
| AU | 2005201044 B2 | 4/2005 |
| DE | 19618797 A1 | 10/1996 |
| DE | 19631919 C2 | 7/1998 |
| DE | 19903713 | 1/1999 |
| DE | 19903713.2 | 1/1999 |
| DE | 19956568.6 | 11/1999 |
| DE | 20023125 U1 | 1/2000 |
| DE | 10100588 A1 | 1/2001 |
| DE | 10163098 A1 | 12/2001 |
| DE | 10230996 A1 | 7/2002 |
| DE | 10230997 A1 | 7/2002 |
| DE | 10235620.3 | 8/2002 |
| DE | 69233117 | 4/2004 |
| DE | 10080167 | 3/2008 |
| DE | 100 66 235 | 4/2008 |
| EP | 1214945 A2 | 1/2000 |
| EP | 1144623 B1 | 8/2002 |
| EP | 1230375 B1 | 7/2005 |
| EP | 1550719 A1 | 7/2005 |
| EP | 1550719 B1 | 12/2008 |
| GB | 9927444.1 | 11/1999 |
| WO | WO 89/02468 | 3/1989 |
| WO | WO 89/05345 | 6/1989 |
| WO | WO 89/07136 | 8/1989 |
| WO | WO 92/07573 | 5/1992 |
| WO | WO 92/19732 | 11/1992 |
| WO | WO 94/01550 | 1/1994 |
| WO | WO 96/17057 | 6/1996 |
| WO | WO 97/05266 A1 | 2/1997 |
| WO | WO 97/43431 | 11/1997 |
| WO | WO 98/05770 A3 | 2/1998 |
| WO | WO 98/53083 | 11/1998 |
| WO | WO 99/15682 | 4/1999 |
| WO | WO 99/32619 | 7/1999 |
| WO | WO 99/49029 | 9/1999 |
| WO | WO 99/53050 | 10/1999 |
| WO | WO 99/54459 | 10/1999 |
| WO | WO 99/61631 | 12/1999 |
| WO | WO 00/01846 | 1/2000 |
| WO | WO 00/22113 | 4/2000 |
| WO | WO 00/22114 | 4/2000 |
| WO | WO 00/44495 | 8/2000 |
| WO | WO 00/44895 | 8/2000 |
| WO | WO 00/44914 | 8/2000 |
| WO | WO 00/63364 | 10/2000 |
| WO | WO 00/68374 | 11/2000 |
| WO | WO 01/18197 A1 | 3/2001 |
| WO | WO 01/29058 A1 | 4/2001 |
| WO | WO 01/36646 | 5/2001 |
| WO | WO 01/36646 A1 | 5/2001 |
| WO | WO 01/42443 A1 | 6/2001 |
| WO | WO 01/48183 A2 | 7/2001 |
| WO | WO 01/68836 A2 | 9/2001 |
| WO | WO 01/70949 A1 | 9/2001 |
| WO | WO 01/75164 A2 | 10/2001 |
| WO | WO 01/92513 A1 | 12/2001 |
| WO | WO 02/16620 A2 | 2/2002 |
| WO | WO 02/26780 A2 | 4/2002 |
| WO | WO 02/44321 A2 | 6/2002 |
| WO | WO 02/055692 A2 | 7/2002 |
| WO | WO 02/055693 A2 | 7/2002 |
| WO | WO 02/061034 A2 | 8/2002 |
| WO | WO 02/068635 A2 | 9/2002 |
| WO | WO 02/068637 A2 | 9/2002 |
| WO | WO 03/006477 A1 | 1/2003 |
| WO | WO 03/012052 A2 | 2/2003 |
| WO | WO 03/012082 A2 | 2/2003 |
| WO | WO 03/016572 A1 | 2/2003 |
| WO | WO 03/033700 A1 | 4/2003 |
| WO | WO 03/035082 A1 | 5/2003 |
| WO | WO 03/035083 A1 | 5/2003 |
| WO | WO 03/035868 A1 | 5/2003 |
| WO | WO 03/035869 A1 | 5/2003 |
| WO | WO 03/035870 A1 | 5/2003 |
| WO | WO 03/035876 A1 | 5/2003 |
| WO | WO 03/040366 | 5/2003 |
| WO | WO 03/070283 A2 | 8/2003 |
| WO | WO 03/070750 A2 | 8/2003 |
| WO | WO 03/070969 A2 | 8/2003 |
| WO | WO 03/070972 A2 | 8/2003 |
| WO | WO 03/074654 A2 | 9/2003 |
| WO | WO 03/080794 A2 | 10/2003 |
| WO | WO 03/080807 A2 | 10/2003 |
| WO | WO 2004/015107 | 2/2004 |
| WO | WO 2004/027030 | 4/2004 |
| WO | WO 2004/045543 | 6/2004 |
| WO | WO 2004/065601 | 8/2004 |
| WO | WO 2005/012357 | 5/2005 |

OTHER PUBLICATIONS

U.S. Appl. No. 60/117,335, Li et al. (filed Jan. 28, 1999).
U.S. Appl. No. 60/130,377, Pachuk et al. (filed Apr. 21, 1999).
Agrawal et al., "Self-Stabilized Oligonucleotides as Novel Antisense Agents," *Delivery Strategies for Antisense Oligonucleotide Therapeutics*, Edited by Saghir Akhtar, CRC Press, pp. 105-121 (1995).
Agrawal et al., 1995, 105-21, Editors: Akhtar, Saghir, Publisher CRC.
Ambros, V., (2001), "Dicing Up RNAs", *Science*, 293:811-813.
Asanuma, H. et al., (1999), "Photoregulation der Bildung and Dissoziation eines DNA-Duplexes durch *cis-trans*-Isomerisierung einer Azobenzoleinheit", *Angew. Chem.*, 111:2547-2549.
Ausubel, F. et al. (1999) Supplement 48, pp. 9.4.7. to 9.4.8.
Azhayeva, E. et al., (1997), "Inhibitory properties of double helix forming circular oligonucleotides", *Nucl. Acids Res.*, 25:4954-4961.
Bahramian et al.; Molecular and Cellular Biology, vol. 19:274-283, Transcriptional and Posttranscriptional Silencing of Rodent α1(I) Collagen by a Homologous Transcriptionally Self-Silenced Transgene Jan. 1999.
Barwkar, D.A. et al.; Proc. Natl. Acad. Sci USA, vol. 95:11047-11052, Sep. 1998, Chemistry, Biochemistry.
Bass, B.L., (2000), "Double-Stranded RNA as a Template for Gene Silencing", *Cell*, 101:235-238.
Bhan et al., Nucleic Acid Research, 1997; vol. 25; p. 3310.
Billy, et al. (2001) PNAS 98(25):14428-33.
Borecky et al. (1981-82) Tex Rep Biol Med 41:575-81 Abstract Only.
Barber et al., "Mutants of the RNA-Dependent Protein Kinase (PKR) Lacking Double-Stranded RNA Binding Domain I Can Act as Transdominant Inhibitors and Induce Malignant Transformation," *Mol. Cell. Biol.*, 15(6):3138-3146 (1995).
Braich et al., "Regiospecific Solid-Phase Synthesis of Branched Oligonucleotides. Effect of Vicinal 2',5'-(or 2',3'-) and 3',5'-Phosphodiester Linkages on the Formation of Hairpin DNA," *Bioconjug. Chem.*, 8:370-377 (1997).

Brennicke et al., "RNA editing," *FEMS Microbiology Reviews*, 23:297-316 (1999).
Byrom et al., "Inducing RNAi with siRNA Cocktails Generated by RNase III," *TechNotes* 10(1), Ambion, http://www.ambion.com/techlib/tn/101/4.html (2004).
Castelli, J. et al., (998), "The 2-5A system in viral infection and apoptosis", *Biomed. Pharmacother.*, 52:386-390.
Cobaleda, C. et al., (2000), "In vivo inhibition by a site-specific catalytic RNA subunit of Rnase P designed against the BCR-ABL oncogenic products: a novel approach for cancer treatment", *Blood*, 95(3):731-737.
Chien et al., "Novel cationic cardiolipin analogue-based liposome for efficient DNA and small interfering RNA delivery in vitro and in vivo," *Cancer Gene Therapy*, pp. 1-8 (2004).
Couzin, "Small RNAs Make Big Splash," *Science*, 298:2296-2297 (2002).
Czauderna et al., "Structural variations and stabilizing modifications of synthetic siRNAs in mammalian cells," *Nucleic Acids Res.*, 31(11):1-12 (2003).
Caplen, N.J., (2002), "A new approach to the inhibition of gene expression", *TRENDS in Biotechnology*, 20(2):49-51.
Caplen, N.J. et al., (2001), "Specific inhibition of gene expression by small double-stranded RNAs in invertebrate and vertebrate systems", *Proc. Natl. Acad. Sci. USA*, 98(17):9742-9747.
Datenbank MEDLINE bei STN: AN 1999091059 MEDLINE; DN 99091059 zu: Use of dsRNA-mediated genetic interference to demonstrate that frizzled and frizzled 2 act in the wingless pathway. Kennerdell J.R.; Carthew R.W.; Cell, (Dec. 23, 1998) 95(7):1017-1026.
Downward, J. et al., (1990), "Identification of a nucleotide exchange-promoting activity for p21$^{ras}$", *Proc. Natl. Acad. Sci. USA*, 87:5998-6002.
Dellweg et al., ed., *Römpp Lexikon Biotechnologie*, p. 354 and p. 673 (1992) (in German).
Doench, J.G. et al., (2003), "siRNAs can function as miRNAs", *Genes & Development*, 17:438-442.
Donzé, O. et al., (2002), "RNA interference in mammalian cells using siRNAs synthesized with T7 RNA Polymerase", *Nucleic Acids Research*, 30(10):e46(4pages).
Elbashir et al., "Analysis of gene function in somatic mammalian cells using small interfering RNAs," *Methods*, 26:199-213 (2002).
Elbashir, S.M. et al., (2001), "RNA interference is mediated by 21- and 22-nucleotide RNAs", *Genes & Development*, 15:188-200.
Elbashir, S.M. et al., (2001), "Functional anatomy of siRNAs for mediating efficient RNAi in *Drosophila melanogaster* embryo lysate", *The EMBO Journal*, 20(23):6877-6888.
Elbashir, et al. (2001) Nature 411:494-498.
Fallert-Müller, ed., *Encyclopedia of Biochemistry*, vol. J-Z, pp. 448-449 (2000) (in German).
Fire, A. et al., (1998), "Potent and specific genetic interference by double-stranded RNA in *Caenorhabditis elegans*", *Nature*, 391:806-811.
Fire, Sep. 1999, *RNA-triggered gene silencing*, Trends Genet, 15: 358-363.
Fire, A., et al., 1991, *Production of Antisense RNA leads to effective and specific inhibition of gene expression in C. elegans muscle*, Development 113: 503-514.
Gautschi, O. et al., (2001), "Activity of a Novel bcl-2/bcl-xL-Bispecific Antisense Oligonucleotide Against Tumors of Diverse Histologic Origins", *Journal of the National Cancer Institute*, 93(6):463-471.
Gibbs, J.B. et al., (1988), "Purification of ras GTPase activating protein from bovine brain", *Proc. Natl. Acad. Sci. USA*, 85:5026-5030.
Grasby, JA et al.; Biochemistry Mar. 28, 1995; 34(12);4068-76.
Griffey, RH et al.; J Med Chem Dec. 20, 1996; 39(26);5100-9.
Gryaznov et al., "Template controlled coupling and recombination of oligonucleotide blocks containing thiophosphoryl groups," *Nucleic Acids Res.*, 21(6):1403-1408 (1993).
Ha, I et al.; Genes Dev Dec. 1, 1996;10(23);3041-50.
Hamilton et al.; Science, vol. 286:950-951, A Species of Small Antisense RNA in Posttranscriptional Gene Silencing in Plants (Oct. 29, 1999).

Hammond, S.M. et al., (2000), "An RNA-directed nuclease mediates post-transcriptional gene silencing in *Drosophila* cells", *Nature*, 404:293-296.
Hoke, GD et al.; Nucleic Acids Res Oct. 25, 1991; 19(20):5743-8.
Harborth, J. et al., (2001), "Identification of essential genes in cultured mammalian cells using small interfering RNAs", *Journal of Cell Science*, 114(24):4557-4565.
Hedges, "The Origin and Evolution of Model Organisms," *Nature Reviews*, 3:838-849 (2002).
Hornung et al., "Sequence-specific potent induction of IFN-60 by short interfering RNA in plasmacytoid dendritic cells through TLR7," *Nature Medicine*, 11(3):263-270 (2005).
Hu-Lieskovan et al., "Sequence-Specific Knockdown of EWS-FLI1 by Targeted, Nonviral Delivery of Small Interfering RNA Inhibits Tumor Growth in a Murine Model of Metastatic Ewing's Sarcoma" *Cancer Res.*, 65(19):8984-8992 (2005).
Hunter et al., "The characteristics of inhibition of protein synthesis by double stranded ribonucleic acid in reticulocyte lysates," *J. Biol. Chem.*, 250(2):409-417 (1975).
Holen, T. et al., (2002), "Positional effects of short interfering RNAs targeting the human coagulation trigger Tissue Factor", *Nucleic Acids Research*, 30(8):1757-1766.
Horn, T et al.; Nucleic Acids Research, 1997, vol. 25, No. 23 : 4842-4849.
Hunter, Jun. 17, 1999, *A touch of elegance with RNAi*, Curr Biolo, 9: R440-R442.
"InBase, The Intein Database: The Intein Registry—Inteins Sorted by Species," http://tools.neb.com/inbase/list.php (database updated on May 22, 2006).
International Preliminary Examination Report from PCT/DE00/00244.
"Introduction of DNA into Mammalian Cells," *Current Protocols in Molecular Biology*, Supplement 48, Edited by Frederick M. Ausubel et al., John Wiley & Sons, Inc., pp. 9.4.7-9.4.8 (1999).
Iwase, R et al.; Nucleic Acids Symp Ser 1997; (37);203-4.
International Search Report PCT/DE 00/00244.
Jacobs, B.L., and Langland, J.O., 1996, *When two stands are better than one: The mediators and modulators of the cellular responses to double-stranded RNA*. Virology 219: 339-349.
Judge et al., "Sequence-dependent stimulation of the mammalian innate immune response by synthetic siRNA," *Nat. Biotechnol.*, pp. 1-6 (2005) (8 pages of supplementary content included).
Kennerdell et al.; Cell, vol. 95, S. 1017-1026; "Use of dsRNA-Mediated Genetic Interference to Demonstrate that frizzled and frizzled 2 Act in the Wingless Pathway" Dec. 23, 1998.
Klemens, et al.(1999), *The 2 Å Structure of helix 6 of the human signal recognition particle RNA.*, Structure 7(11): 1345-1352.
Kreutzer et al (1999) Gesellschaft fur Biochemie und Molekularbiologie S169.
Kitabwalla et al., "RNA-Interference—A New Weapon Against HIV and Beyond," *N. Engl. J. Med.*, 347(17):1364-1367 (2002).
Madhur Kumar et al. "Antisense RNA: Function and Fate of Duplex RNA in Cells of Higher Eukaryotes" Microbiology and Molecular Biology Reviews, vol. 62, Dec. 1998, pp. 1415-1434.
Lee et al., "The *C. elegans* Heterochronic Gene *lin-4* Encodes Small RNAs with Antisense Complementarity to *lin-14*," *Cell*, 75:843454 (1993).
Letter to the International Examining Authority from Gassner & Partner in the prosecution of PCT/DE00/00244 (WO 00/44895), 5 pages (Mar. 28, 2001) (in German).
Lewis, D.L. et al., (2002), "Efficient delivery of siRNA for inhibition of gene expression in postnatal mice", *Nature Genetics*, 32:107-108.
Lee, et al.; Cell, vol. 88; S. 637-646; Mar. 7, 1997; The Cold Shock Domain Protein LIN-28 Controls Developmental Timing in *C. elegans* and is Regulated by the lin-4 RNA.
Li et al., Dev. Biology vol. 210, 1999, p. 238 abstract 346.
Lin et al.; Nature, vol. 402:128-129, "Policing rogue genes" Nov. 11, 1999.
Lipardi, C. et al., (2001), "RNAi as Random Degradative PCR: siRNA Primers Convert mRNA into dsRNAs that are Degraded to Generate New siRNAs", *Cell*, 107:297-307.
Lipinski, et al. (1997) Adv. Drug Delivery Review 23:3-25.

Lowy, D.R. et al., (1993), "Function and Regulation of RAS", *Annu. Rev. Biochem.*, 62:851-891.

Manche, L. et al., (1992), "Interactions between Double-Stranded RNA Regulators and the Protein Kinase DAI", *Molecular and Cellular Biology*, 12(11):5238-5248.

McCaffrey, A.P. et al., (2002), "RNA interference in adult mice", *Nature*, 418:38-39.

Ma MY (1993) Biochem. 32(7):1751-8.

Majumdar, A et al.; Nat Genet Oct. 1998; 20(2):212-4.

Milhaud et al., Journal of Interferon Research, 1991, vol. 11, 261-265.

Minks, M. A. et al., The Journal of Biological Chemistry (1979), 254, (20):10180-10183.

Montgomery, M., and Fire, 1998, *Analysis of a Caenorhabditis elegans twist homolog identifies conserved and divergent aspects of mesodermal patterning*, Genes and Development, 12: 2623-2635.

Montgomery M.K., et al., 1998, *RNA as a target of double-stranded RNA-mediated genetic interference in Caenorhabditis elegan*, Proc. Natl. Acad. Sci. 95: 15502-15507.

Montgomery, et al., Jul. 1998, *Double-stranded RNA as a mediator in sequence-specific genetic silencing and co-suppression*, TIG, vol. 14, No. 7., pp. 255-258.

Misquitta, L. and Paterson, B.M., 1999, *Targeted disruption of gene function in Drosophila by RNA interference (RNA-i): A role for nautilus in embryonic somatic muscle formation*, Proc. Natl. Acad. Sci. 96: 1451-1456.

Marques et al., "Activation of the mammalian immune system by siRNAs," *Nat. Biotechnol.*, 23(11):1399-1405 (2005).

Martinez et al., "Single-Stranded Antisense siRNAs Guide Target RNA Cleavage in RNAi," *Cell*, 110:563-574 (2002).

McManus et al., "Gene Silencing in Mammals by Small Interfering RNAs," *Nat. Rev. Genet.*, 3:737-747 (2002).

Moss et al., "The Cold Shock Domain Protein LIN-28 Controls Developmental Timing in *C. elegans* and is Regulated by the *lin-4* RNA," *Cell*, 88:637-646 (1997).

Neilsen et al. (1997) Chem. Comm. 825-826.

Ngo, H., et al., 1998, *Double-stranded RNA induces mRNA degradation in Trypanosoma brucei*, Proc Natl. Acad. Sci. 95: 14687-14692.

Nikiforov, et al. (1992) Nucleic Acids Research 20(6):1209-1214.

Nielsen et al., "A novel class of conformationally restricted oligonucleotide analogues: synthesis of 2',3'-bridged monomers and RNA-selective hybridization," *Chem. Commun.*, pp. 825-826 (1997).

Paddison, P.J. et al., (2002), "Short hairpin RNAs (shRNAs) induce sequence-specific silencing in mammalian cells", *Genes & Development*, 16:948-958.

PCT/GB00/04404 as filed (Nov. 19, 1999).

Pegram, MD et al.; J. Clin Oncol Aug. 1998; 16(8):2659-71.

Pegram et al., "Phase II Study of Receptor-Enhanced Chemosensitivity Using Recombinant Humanized Anti-p185$^{HER2/neu}$ Monoclonal Antibody Plus Cisplatin in Patients With HER2/neu-Overexpressing Metastatic Breast Cancer Refractory to Chemotherapy Treatment," *J. Clin. Oncol.*, 16(8):2659-2671 (1998).

Perler, "InBase: the Intein Database," *Nucleic Acids Res.*, 30(1):383-384 (2002).

Regalado, "Turning Off Genes Sheds New Light on How They Work," *The Wall Street Journal*, 4 pages (Aug. 6, 2002).

Robbins et al., "Sensing the danger in RNA," *Nat. Med.*, 11(3):250-251 (2005).

Randall, G. et al., (2003), "Clearance of replicating hepatitis C virus replicon RNAs in cell culture by small interfering RNAs", *PNAS*, 100(1):235-240.

Ravinderjit, et al. (1997) Bioconjugate Chem. 8:370-377.

Rosalind C. Lee, et al.; Cell, vol. 75, 843-854, Mar. 12, 1993; "The *C. elegans* Herochronic Gene lin-4 Encodes Small RNAs with Antisense Complementary to lin-14".

Seydoux, G., et al., 1996, *Repression of gene expression in the embryonic germ lineage of C. elegans*. Nature 382: 713-716.

Sharp, P.A., (2001), "RNA interference—2001", *Genes & Development*, 15:485-490.

Sharp, P.A., 1999, *RNAi and double-stranded RNA*. Gene and Development 13: 139-141.

Sijen, T. et al., (2001), "On the Role of RNA Amplification in dsRNA-Triggered Gene Silencing", *Cell*, 107:465-476.

Strauss; Science, vol. 286:886; "Candidate 'Gene Silencers' Found" Oct. 29, 1999.

Schwarz et al., "Evidence that siRNAs Function as Guides, Not Primers, in the *Drosophila* and Human RNAi Pathways," *Mol. Cell*, 10:537-548 (2002).

Sharp et al., "RNAi and double-strand RNA," *Genes Dev.*, 13:139-141 (1999).

Shi et al., "A CBP/p300 homolog specifies multiple differentiation pathways in *Caenorhabditis elegans*," *Genes Dev.*, 12:943-955 (1998).

Sinha, "Large-scale Synthesis. Approaches to Large-scale Synthesis of Oligodeoxynucleotides and their Analogs," *Antisense—From Technology to Therapy*, vol. 6, Edited by Reimar Schlingensiepen et al., pp. 29-58 (1997).

Skripkin et al., "Psoralen crosslinking between human immunodeficiency virus type 1 RNA and primer tRNA$_3^{Lys}$," *Nucleic Acids Res.*, 24(3):509-514 (1996).

Sledz et al., "Activation of the interferon system by short-interfering RNAs," *Nat. Cell Biol.*, 5(9):834-839 (2003).

Soutschek et al., "Therapeutic silencing of an endogenous gene by systemic administration of modified siRNAs," *Nature*, 432:173-178 (2004).

Strauss, "Candidate 'Gene Silencers' Found," *Science*, 286:886 (1999).

Timmons et al., "Specific interference by ingested dsRNA," *Nature*, 395:854 (1998).

Tuschl et al., "Targeted mRNA degradation by double-stranded RNA in vitro," *Genes Dev.*, 13:3191-3197 (1999).

Tijsterman, M. et al., (2002), "The Genetics of RNA Silencing", *Annu. Rev. Genet.*, 36:489-519.

James D. Thompson, Dec. 1999, *Shortcuts from gene sequence to function*, Nature Biotechnology, vol. 17, pp. 1158-1159.

Timmons et al.; Nature, 395(6705:854); "Specific Interference by Ingested dsRNA" Oct. 29, 1998.

Tuschl et al. (Dec. 1999) Genes and Dev. 13:3191-7.

Uhlmann, E. et al. "Antisense Nucleotides: A New Therapeutic Principal" Chemical Reviews, American Chemical Society, Easton, US vol. 90, No. 4, Jun. 1, 1990, pp. 543-584, ISSN:0009-2665.

Voinnet et al., "Systemic signalling in gene silencing," *Nature*, 389:553 (1997).

Voinnet, O. and Baulcombe, D. C., Nature (1997), 398:553.

Wagner, et al., Feb. 19, 1998, *Double-stranded RNA poses puzzle*, Nature; 391: 744-745.

Wargelius, et al., 1999, *Double-stranded RNA induces specific developmental defects in zebrafish embryos*, Biochem Biophys Res Com., 263: 156-161.

Waterhouse et al.; PNAS, vol. 95:13959-13964, "Virus resistance and gene silencing in plants can be induced by simultaneous expression of sense and antisense RNA" Nov. 1998.

Wianny, et al. (2000) Nature Cell Biology 2:70-75.

Wild, K. et al., (1999), "The 2 Å structure of helix 6 of the human signal recognition particle RNA", *Structure*, 7(11):1345-1352.

Wargelius et al., "Double-Stranded RNA Induces Specific Developmental Defects in Zebrafish Embryos," *Biochem. Biophys. Res. Commun.*, 263:156-161 (1999).

Waterhouse et al., "Virus resistance and gene silencing in plants can be induced by simultaneous expression of sense and antisense RNA," *Proc. Natl. Acad. Sci. USA*, 95:13959-13964 (1998).

Wess et al., "Early days for RNAi," *BioCentury*, 11(12):A1-A8 (2003).

Wianny et al., "Specific interference with gene function by double-stranded RNA in early mouse development," *Nat. Cell Biol.*, 2:70-75 (2000).

Yang, D. et al., (2000), "Evidence that processed small dsRNAs may mediate sequence-specific mRNA degradation during RNAi in *Drosophila* embryos", *Current Biology*, 10:1191-1200.

Yang Shi, et al.; Genes & Development, vol. 12, (No. 7):943-955; "A CBP/p300 homolog specifies multiple differentiation pathways in *Caenorhabditis elegans*" Apr. 1, 1998.

Yu, J. et al., (2002), "RNA interference by expression of short-interfering RNAs and hairpin RNAs in mammalian cells", PNAS, 99(9):6047-6052.

Zamore et al., "RNAi: Double-Stranded RNA Directs the ATP-Dependent Cleavage of mRNA at 21 to 23 Nucleotide Intervals," Cell, 101:25-33 (2000).

Zeng et al., "RNA interference in human cells is restricted to the cytoplasm," RNA, 8:855-860 (2002).

Zhao et al., "Double-Stranded RNA Injection Produces Nonspecific Defects in Zebrafish," Dev. Biol., 229:215-223 (2001).

Notice of Opposition by Aventis against European Patent No. 11 44 623 (May 28, 2003).

Notice of Opposition by AstraZeneca against European Patent No. 11 44 623 (May 28, 2003).

Notice of Opposition by Isis Pharmaceuticals against European Patent No. 11 44 623 (May 28, 2003).

Notice of Opposition by Novartis against European Patent No. 11 44 623 (May 28, 2003).

Notice of Opposition by Janssen Pharmaceuticals against European Patent No. 11 44 623 (May 28, 2003).

Submission by Alnylam Europe in opposition proceedings for European Patent No. 11 44 623 (Dec. 7, 2004).

Submission by Sirna Therapeutics in opposition proceedings for European Patent No. 11 44 623 (Apr. 20, 2006—Uexkull & Stolberg).

Submission by Sirna Therapeutics in opposition proceedings for European Patent No. 11 44 623 (Apr. 20, 2006—Isenbruck, Bosl, Horshchler, Wichmann, Huhn).

Submission by Atugen in opposition proceedings for European Patent No. 11 44 623 (Apr. 21, 2006).

Submission by Alnylam Europe in opposition proceedings for European Patent No. 11 44 623 (Apr. 21, 2006).

Submission by Alnylam Europe in opposition proceedings for European Patent No. 11 44 623 (Jun. 7, 2006).

Minutes of the Oral Proceedings in opposition proceedings for European Patent No. 11 44 623 (Jun. 22, 2006).

Interlocutory Decision and Druckexemplar in opposition proceedings for European Patent No. 11 44 623 (Sep. 25, 2006).

Submission by Alnylam Europe in opposition proceedings for European Patent No. 11 44 623 (Jun. 25, 2007).

Submission by Sirna Therapeutics in opposition to European Patent No. 1 144 623 (Jun. 12, 2008).

Communication of Technical Board of Appeal in opposition to European Patent No. 1 144 623 (Sep. 22, 2008). (translation attached).

Submission by Atugen AG in opposition to European Patent No. 1 144 623 (Nov. 7, 2008).

Submission by Sirna Therapeutics in opposition to European Patent No. 1 144 623 (Nov. 6, 2008).

Submission by Alnylam Pharmaceuticals in the opposition proceedings of European Patent No. 1 144 623 (Nov. 7, 2008). (translation attached).

Notice of opposition by Quark Biotech against European Patent No. 1 214 945 (Mar. 7, 2006).

Notice of opposition by Sirna Therapeutics against European Patent No. 1 214 945 (Mar. 7, 2006).

Notice of opposition by Abbott Laboratories against European Patent No. 1 214 945 (Mar. 8, 2006).

Zheng et al., "Activation of the protein kinase PKR by short double-stranded RNAs with single-stranded tails," RNA, 10:1934-1945 (2004).

International Search Report of International Application No. PCT/EP02/00151.

Notice of Opposition to European Patent Application No. EP 05002454.6, filed by SIRNA Therapeutics, filed on Sep. 21, 2009, 42 Pages.

Decision to revoke European Patent EP 1144623 of Alnylam Europe AG, Dec. 19, 2008, 50 Pages.

Decision to revoke European Patent EP 1214945 of Alnylam Europe AG, Jan. 20, 2009, 56 Pages.

Decision to revoke European Patent EP 10080167 of Alnylam Europe AG, Mar. 18, 2009, 26 Pages.

Office Action for U.S. Appl. No. 10/382,395, Oct. 5, 2009, 9 Pages.

Office Action for U.S. Appl. No. 10/383,099, Dec. 17, 2009, 9 Pages.

Office Action for U.S. Appl. No. 10/382,768, Feb. 5, 2010, 12 Pages.

Notice of Reasons for Rejection for Japan Patent Application No. 2009-002824, Jun. 16, 2009, 15 Pages.

Notice of Reasons for Rejection for Japan Patent Application No. 2009-002826, Jun. 16, 2009, 15 Pages.

Jiang, A., et al., "In vivo cell type-specific gene delivery with retroviral vectors that display single chain antibodies," Gene Therapy, 1999, pp. 1982-1987, vol. 6.

Lubberts, E., et al., "Adenoviral Vector-Mediated Overexpression of IL-4 in the Knee Joint of Mice with Collagen-Induced Arthritis Prevents Cartilage Destruction," The Journal of Immunology, 1999, pp. 4546-4556.

Nishi, T., et al., "High-Efficiency in Vivo Gene Transfer Using Intraarterial Plasmid DNA Injection following in Vivo Electroporation," Cancer Research, Mar. 1, 1996, pp. 1050-1055, vol. 56.

Niu, G., et al., "Gene Therapy with Dominant-negative Stat3 Suppresses Growth of the Murine Melanoma B16 Tumor in Vivo," Cancer Research, Oct. 15, 1999, pp. 5059-5063, vol. 59.

Xie, Y., et al., "Efficacy of Adenovirus-mediated CD/5-FC and HSV-I Thymidine Kinase/Ganciclovir Suicide Gene Therapies Concomitant with p53 Gene Therapy," Clinical Cancer Research, Dec. 1999, pp. 4224-4232, vol. 5.

Decision of Rejection for Japan Patent Application No. 2009-002824, Mar. 9, 2010, 4 Pages.

Decision of Rejection for Japan Patent Application No. 2009-002826, Mar. 9, 2010, 4 Pages.

Auszug aus der online-Rolle des EPA, Excerpt from the European Patent Register for EP 1147204, Database last updated on Jun. 18, 2008, 4 Pages.

Communication in opposition proceedings for German Patent No. 10066235.8 (Jun. 23, 2009).

Document by Sirna Therapeutics et al. in opposition proceedings for German Patent No. 10066235.8 (Dec. 9, 2008).

Petition by Pfizer Inc. in opposition proceedings for German Patent No. 10066235.8 (May 25, 2008).

Petition by Sanofi-Aventis et al. in opposition proceedings for German Patent No. 10066235.8 (May 22, 2008).

Petition by Silence Therapeutics in opposition proceedings for German Patent No. 10066235.8 (May 25, 2008).

Damha, M., et al., "Chapter 5: Oligoribdonucleotides synthesis: the silyl-phosphoramidite method," Methods in Molecular Biology 20, Humana Press NJ: 81-114 (1993).

Gait, M., "Chapter 16: Oligoribdonucleotides," Antisense Research and Applications, CRC Press 289-302, 1993.

Sproat, B., "Chapter 6: Synthesis of 2'-O-Alkyloligoribonucleotides," Methods in Molecular Biology 20, Humana Press, NJ: 115-142, 1993.

Sproat, B., "Chapter 18: 2-O-Alkyloligoribonucleotides," Antisense Research and Applications, CRC Press, 351-362, 1993.

Notice of Opposition by Sirna Therapeutics against European Patent No. 11 44 623 (May 19, 2003).

Notice of Opposition by Dr. Martin Grund against European Patent No. 11 44 623 (May 28, 2003).

Notice of Opposition by Atugen AG against European Patent No. 11 44 623 (May 28, 2003).

Notice of opposition by Atugen against European Patent No. 1 214 945 (Mar. 8, 2006).

Reply to notice of opposition by Alnylam Europe in the opposition proceedings of European Patent No. 1 214 945 (Dec. 28, 2006).

Submission by Abbott Laboratories in the opposition proceedings of European Patent No. 1 214 945 (Oct. 30, 2007).

Submission by Sirna Therapeutics in the opposition proceedings of European Patent No. 1 214 945 (Jan. 4, 2008).

Summons to attend oral proceedings in the opposition proceedings of European Patent No. 1 214 945 (May 6, 2008).

Submission by Alnylam Pharmaceuticals in the opposition proceedings of European Patent No. 1 214 945 (Nov. 20, 2008).

Submission by Sirna Therapeutics in the opposition proceedings of European Patent No. 1 214 945 (Nov. 20, 2008).

Submission by Silence Therapeutics in the opposition proceedings of European Patent No. 1 214 945 (Nov. 20, 2008).

Submission by Abbott Laboratories in the opposition proceedings of European Patent No. 1 214 945 (Nov. 20, 2008).

Response to Official Action filed for Australian Application No. 32713/00 (Oct. 19, 2004).
Statement of Grounds and Particulars of Opposition to Australian Patent No. 778474, filed by Sirna Therapeutics, Inc. (Jun. 9, 2005).
Petition submitted by Alnylam Europe AG against DE 100 80 167.6, including claims as filed and list of documents cited (Dec. 18, 2008).
Notice of Opposition by Alexandra Oppl against DE 100 80 167.6 (Jun. 20, 2008).
Notice of Opposition by Pfizer against DE 100 80 167.6 (Jun. 19, 2008).
Notice of Opposition by Sanofi Aventis against DE 100 80 167.6 (Jun. 16, 2008).
Notice of Opposition by Silence Therapeutics against DE 100 80 167.6 (Jun. 20, 2008).
Notice of Opposition by Sirna against DE 100 80 167.6 (Jun. 20, 2008).
Submission by Alexandra Oppl in opposition to DE 100 80 167.6 (Jun. 20, 2008).
Submission by Sirna Therapeutics in opposition to DE 100 80 167.6 (Jun. 20, 2008).
Decision by German Patent Office in opposition proceedings for DE 100 80 167.6 (Feb. 17, 2009).
Submission by Silence Therapeutics against DE 100 80 167.6 on Feb. 20, 2009.
Submission by Pfizer against DE 100 80 167.6 on Feb. 27, 2009.
Submission by Alnylam Europe AG in opposition to DE 100 80 167.6 on Mar. 4, 2009.
Submission by Alexandra Oppl against DE 100 80 167.6 on Mar. 4, 2009.
Submission by SIRNA Therapeutics against DE 100 80 167.6 on Mar. 4, 2009.
Response to three Notices of Opposition submitted by Alnylam Europe AG in German Patent No. 100 66 235.8-41 (Feb. 4, 2009), including list of documents cited (translation enclosed).
Notice of Opposition to German Application No. DE 100 66 235, filed by Silence Therapeutics AG on Jul. 10, 2008.
Notice of Opposition to German Application No. DE 100 66 235, filed by Sanofi Aventis Deutschland GmbH on Jul. 10, 2008.
Notice of Opposition to German Application No. DE 100 66 235, filed by Pfizer Inc. on Jul. 9, 2008.
List of Documents in Oppositions to German Application No. DE 100 66 235, filed by Silence Therapeutics AG, Sanofi Aventis Deutschland GmbH, and Pfizer Inc.
Statement of Grounds and Particulars of Opposition to Australian Patent No. 778474, filed by SIRNA Therapeutics, Inc. on Sep. 9, 2005.
Statutory Declaration by Martin Edward O'Brien of Spruson and Ferguson in the matter of Opposition to Australian Patent No. 778474, filed by SIRNA Therapeutics, Inc. on Sep. 9, 2005.
Agami, "RNAi and related mechanisms and their potential use for therapy" Current Opin. Chem. Biol. 6:829-834 (2002).
Agrawal et al., "Antisense therapeutics: is it as simple as complementary base recognition?" Molecule Medicine 6:72-81 (2000).
Alfonzo et al., "The mechanism of U insertion/deletion RNA editing in kinetoplastid mitochondria" Nucleic Acid Res. 25:3751-3759 (1997).
Anderson, "Human gene therapy" Nature 392:25-30 (1998).
Armentano et al., "Expression of human factor IX in rabbit hepatocytes by retrovirus-mediated gene transfer: Potential for gene therapy of hemophilia B" Proc. Natl. Acad. Sci USA 87:6141-6145 (1990).
Barlow et al., "Interferon synthesis in the early post-implantation mouse embryo" Differentiation 27:229-235 (1984).
Basbaum et al., "Focalized proteolysis: spatial and temporal regulation of extracellular matrix degradation at the cell surface" Curr. Opin. Cell Biol. 8:731-738 (1996).
Beck, "Unknotting the Complexities of Multidrug Resistance: The Involvement of DNA Topoisomerases in Drug Action and Resistance" J. Natl. Cancer Inst. 81:1683-1685 (1989).
Berkner et al., "Development of Adenovirus Vectors for the Expression of Heterologous Genes" BioTechniues 6:616-629 (1998).
Birkedal-Hansen et al., "Matrix Metalloproteinases: A Review" Crit. Rev. Oral Biol. Med. 4:197-250 (1993).
Boese et al., "Mechanistic Insights Aid Computational Short Interfering RNA Design" Methods in Enzymology 392:73-95 (2005).
Boyd, "Invasion and metastasis" Cancer Metastasis Rev. 15:77-89 (1996).
Braasch et al., "Locked nucleic acid (LNA): fine-tuning the recognition of DNA and RNA" Chem. Biol. 8:1-7 (2001).
Branch, "A good antisense molecule is hard to find" TIBS 23:45-50 (1998).
Bruening, "Plant Gene Silencing Regularized" Proc. Natl Acad Science 95:13349-13351 (1998).
Brinckerhoff et al., "Matrix metalloproteinases: a tail of a frog that became a prince" Nature Reviews 3:207-214, (2002).
Bucchini et al., "Pancreatic Expression of Human Insulin Gene in Transgenic Mice" PNAS USA 83:2511-1515 (1986).
Burke et al., "Appearance of Interferon Inducibility and Sensitivity during Differentiation of Murine Teratocarcinoma Cells in vitro" Cell 13:243-248 (1978).
Cameron et al., "Inhibition of Gene Expression by a Short Sense Fragment" Nucleic Acids Research 19:469-475 (1991).
Caplen et al., "dsRNA-Mediated Gene Silencing in Cultured *Drosophila* Cells: a Tissue Culture Model for the Analysis of RNA Interference" Gene 252:95-105 (2000).
Caplen, "RNAi as a gene therapy approach" Expert Opin. Biol. Ther. 3:575-586 (2003).
Chao et al., "BCL-2 Family: Regulators of Cell Death" Arum. Rev. Immunol. 16:395-419 (1998).
Check "RNA to the Rescue?" Nature 425:10-12 (2003).
Chen et al., "Gene therapy for brain tumors: regression of experimental gliomas by adenovirus-mediated gene transfer in vivo" Proc. Natl. Acad. Sci. USA 91:3054-3057 (1994).
Childs et al., "The MDR Superfamily of Genes and Its Biological Implciations" Imp. Adv. Oncol. 21-36 (1994).
Chowdhury et al., "Long-Term Improvement of Hypercholesterolemia After Ex Vivo Gene Therapy in LDLR-Deficient Rabbits" Science 254:1802-1805 (1991).
Cioca et al., "RNA interference is a functional pathway with therapeutic potential in human myeloid leukemia cell lines" Cancer Gene Therapy 10:125-133 (2003).
Coburn et al., "siRNAs: a new wave of RNA-based therapeutics" J. Antimicrobial Chemotherapy 51:753-756 (2003).
Cole et al., "Overexpression of a Transporter Gene in a Multidrug-Resistant Human Lung Cancer Cell Line" Science 258: 1650-1654 (1992).
Cone et al., "High-efficiency gene transfer into mammalian cells: Generation of helper-free recombinant retrovirus with broad mammalian host range" Proc. Natl. Acad. Sci. USA 81:6349-6353 (1984).
Cook, "Medicinal chemistry of antisense oligonucleotides—future opportunities" Anti-Cancer Drug Design 6:585-607 (1991).
Cornetta et al., "Safety Issues Related to Retroviral-Mediated Gene Transfer in Humans" Human Gene Threapy2(1):5-14, 1991.
Cotten et al., "Ribozyme Mediated Destruction of RNA in vivo" EMBO J. 8:3861-3866 (1989).
Couture et al., "Anti-gene therapy: the use of ribozymes to inhibit gene function" Trends in Genetics 12:510-515 (1996).
Crooke et al., "Pharmacokinetic Properties of Several Novel Oligonucleotides Analogs in Mice" J. Pharmacol. Exp. Ther. 277:923-937 (1996).
Crooke, "Basic Principles of Antisense Therapeutics" Antisense Res. and Application Chapter 1, Springer-Verlag, New York (1988).
Dai et al., "Gene therapy via primary myoblasts: Long-term expression of factor IX protein following transplantation in vivo" Proc. Natl Acad. Sci. USA 89:10892-10895 (1992).
Danos et al., "Safe and efficient generation of recombinant retroviruses with amphotropic and ecotropic host ranges" Proc. Natl. Acad. Sci. USA 85:6460-6464 (1998).
D'Ari, "Cycle-regulated genes and cell cycle regulation" Bioassays 23: 563-565 (2001).
Declaration of David M. Stalker filed in opposition proceedings for Australian Patent 778474 (Nov. 4, 2008) (45 pages).
Declaration of David M. Stalker filed in opposition proceedings for Australian Patent 778474 (Nov. 4, 2008) (17 pages).
Declaration of David Keith Myers filed in opposition proceedings for Australian Patent 778474 (Nov. 7, 2008).

Delgado et al., "The Uses and Properties of PEG-Linked Proteins" Crit. Rev. Therap. Drug Carrier Sys. 9:249-304 (1992).
De Fougerolles et al., "RNA interference in vivo: toward synthetic small inhibitory RNA-based therapeutics" Methods in Enzym. 392:278-296 (2005).
Docherty et al., "Nutrient regulation of insulin gene expression" FASEB J. 8:20-27 (1994).
Dolinnaya et al., "Oligonucleotide circulization by temlate-directed chemical ligation" Nucl. Acids Res. 21:5403-5407 (1993).
Eder et al., "Monitoring of BCR-ABL expression using real-time RT-PCR in CML after bone marrow or peripheral blood stem cell transplantation" Leukemia 13:1383-1389 (1999).
Eglitis et al., "Gene Expression in Mice After High Efficiency Retroviral-Mediated Gene Transfer" Science 230:1395-1398 (1985).
Eriksson et al., "Establishment and characterization of mouse stain (TLL) that spontaneously develops T-cell lymphomas/leukemia" Exp. Hematol. 27:682:688 (1999).
Exhibit 1 of David Keith Myers Declaration filed in opposition proceedings for Australian Patent 778474 (Nov. 7, 2008).
Exhibit 2 of David Keith Myers Declaration filed in opposition proceedings for Australian Patent 778474 (Nov. 7, 2008).
Expert-Bezancon et al., "Precise localization of several covalent RNA-RNA cross-link in *Escherichia coli* 16S RNA" European Journal of Biochemistry, 136:267-274 (1983).
Fan et al., "Reversal of Multidrug Resistance in Cancer", ed. Kellen, CRC, Boca Raton, FL, pp. 93-125 (1994).
Ferry et al., "Retroviral-mediated gene transfer into hepatocytes in vivo" Proc. Natl. Acad Sci. USA 88:8377-8381 (1991).
Fire et al., "RNA Interferences—gene silencing by double-stranded RNA" The Nobel Prize in Physiology or Medicine, press release (2006).
Fire et al., "Specific interference by ingested dsRNA" Nature 395:854 (1998).
Fotedar et al., "Apoptosis and the cell cycle" Prog. Cell Cycle Res. 2:147-163 (1996).
Gao et al. "Circularization of oligonucleotides by disulfide bridge formation" Nucl. Acids Res. 23:2025-2029 (1995).
Gassmann et al., "Maintenance of an extrachromosomal plasmid vector in mouse embryonic stem cells" PNAS USA 92:1292-1296 (1995).
M13994: "Human B-cell leukemia/lymphoma 2 (bcl02) proto-oncogene mRNA encoding bcl-2 beta protein," GenBank Record dated Oct. 31, 1994 (GenBank [online] Bethesda, MD, USA: United States National Library of Medicine [retrieved on Aug. 9, 2006]. Retrieved from internet using <URL:http://www.ncbi.nlm.nih.gov/entrez/viewer.fcgi?db=nucleotide&val=179366>, GenBank Accession No. M13994).
M13995: "Human B-cell leukemia/lymphoma 2 (bcl02) proto-oncogene mRNA encoding bcl-2 beta protein," GenBank Record dated Oct. 31, 1994 (GenBank [online] Bethesda, MD, USA: United States National Library of Medicine [retrieved on Aug. 9, 2006]. Retrieved from internet using <URL:http://www.ncbi.nlm.nih.gov/entrez/viewer.fcgi?db=nucleotide&val=179368>, GenBank Accession No. M13995).
U55763: "Cloning vector pEGFP-CA, complete sequence, enhanced green fluorescent protein (egfp) and neomycin phosphotransferase genes," GenBank Record dated Jun. 15, 1996 (GenBank [online] Bethesda, MD, USA: United States National Library of Medicine [retrieved on Aug. 9, 2006]. Retrieved from internet using <URL:http://www.ncbi.nlm.nih.gov/entrez/viewer.fcgi?db=nucleotide&val=1377914>, GenBank Accession No. U55763).
Graessman et al., "Inhibition of SV40 Gene Expression by Microinjected Small Antisense RNA and DNA Molecules" Nucleic Acids Research 19:53-59 (1991).
Graham, "Mapping Transgene Activity in Plants Using Visible Phenotypes" Australian Society for Biochemistry and Molecular Biology Incorporated and Australian Society of Plant Physiologists Incorporated, vol. 28, Abstract SYM-18-06 (1996).
Grierson et al., "Does Co-Suppression of Sense Genes in Transgenic Plants Involve Antisense RNA?" Trends in Biotechnology 9:122-123 (1991).

Green et al., "Antisense Oligonucleotides: An evolving technology for the modulation of gene expression in human disease" J. Am. Coll. Surg. 191:93-105 (2000).
Guang et al., "An Argonaute Transports siRNAs from the Cytoplasm to the Nucleus" Science 321:537-541 (2008).
Guo et al., "Par-1 a Gene Required for Establishing Polarity in C. elegans Embryos, Encodes a Putative Ser/Thr Kinase That is Asymmetrically Distributed" Cell 81:611-620 (1995).
Hamm et al., "Incorporation of 2'-Deoxy-2'mercaptocytidine into Oligonucleotides via Phosphoramidite Chemistry" J. Org. Chem. 62:3415-3420 (1997).
Hanahan et al., "The Hallmarks of Cancer" Cell 100:57-70 (2000).
Harada et al., "Absence of the Type I IFN System in EC Cells: Transcriptional Activator (IRF-1) and Repressor (IRF-2) Genes are Developmentally Regulated" Cell 83:303-312 (1990).
Harfe et al., "Analysis of a Caenorhabditis elegans twist homolog identifies conserved and divergent aspects of mesodermal patterning" Genes and Development 12:2623-2635 (1998).
Harris et al., "The Eu-myc Transgenic Mouse A Model for High-incidence Spontaneous Lymphoma and Leukemia of Early B Cells" J. Exp. Med. 167:353-371 (1988).
Hsu et al., "Immunogencity of Recombinant Adenovirus-Respiratory Syncytial Virus Vaccines with Adenovirus Types 4, 5, and 7 Vectors in Dogs and a Chimpanzee" J. Infectious Disease 166:769-775 (1992).
Huber et al., "Retroviral-mediated gene therapy for the treatment of hepatocellular carcinoma. An innovative approach for cancer therapy" Proc. Natl Acad. Sci USA 88:8039-8043 (1991).
Hwu et al., "Functional and Molecular Characterization of Tumor-Infiltrating Lymphocytes Transduced with Tumor Necrosis Factor-alpha cDNA for the Gene Therapy of Cancer in Humans" J. Immunol. 150:4104-4115 (1993).
Izant et al., "Constitutive and Conditional Suppression of Exogenous and Endogenous Genes by Anti-Sense RNA" Science 229:345-352 (1985).
Jackson et al., Widespread siRNA "off-target" transcript silencing mediated by seed region sequence complementarity, RNA Journal 12:1179-1187 (2007).
Jaschke et al., Nucleosides & Nucleotides 15:1519-1529 (1996).
James et al., "The Therapeutic Potential of Ribozymes" Blood 91:371-382 (1998).
Jennings et al., "Inhibition of SV40 Replicon Function by Engineered Antisense RNA Transcribed by RNA Polymerase III" EMBO Journal 6:3043-3047 (1987).
Jen et al., "Suppression of Gene Expression by Targeted Disruption of Messenger RNA: Available Options and Current Strategies" Stem Cells 18:307-319 (2000).
Jorgensen et al., "Silencing of Plant Genes by Homologous Transgenes" AgBiotech News and Information 4:265-273 (1992).
Kabanov et al., "A new class of antivirals: antisense oligonucleotides combined with a hydrophobic substituent effectively inhibit influenze virus reproduction and synthesis of virus-specific proteins in MDCK cells" FEBS Lett. 259:327-330 (1990).
Kamio et al., "Nucleotide Sequence of an Incompatibility Region of Mini-Rts1 That Contains Five Direct Repeats" Journal of Bacteriology 155:1185-1191 (1983).
Kaufman, "Double-stranded RNA-activated protein kinase-mediates virus-induced apoptosis: A new role for an old actor" *PNAS USA* 96:11693-11695 (1999).
Kay et al., "Hepatic Gene Therapy: Persistent Expression of Human alpha1-Antitrypsin in Mice after Direct Gene Delivery in vivo" Human Gene Therapy 3:641-647 (1992).
Kim et al., "Stable Reduction of Thymidine Kinase Activity in Cells Expressing High Levels of Anti-Sense RNA" Cell 42:129-138 (1985).
Koshkin et al., "LNA (Locked Nucleic Acids) Synthesis of the Adenine, Cytosine, Guanine, 5-Methylcytosine, Thymine and Uracil Biclonucleoside Monomors, Oligomerisation and Unprecedented Nucleic Acid Recognition" Tetrahedron 54:3507-3630 (1998).
Kovalchuk et al., "Burkitt Lymphoma in the Mouse" J. Exp. Med. 192:1183-1190 (2000).
Krepela, "Cysteine proteinases in tumor cell growth and apoptosis" Neoplasma 48:332-349 (2001).

Krieger et al., "The Flavr Savr Tomato, an Early Example of RNAi Technology" HortScience 43:962-964 (2008).
Letsinger et al., "Cholesteryl-conjugated oligonucleotides: Synthesis, properties, and activity as inhibitors of replication of human immunodeficiency virus in cell culture" PNAS USA 86:6553-6556 (1989).
Li et al., "Folate-Mediated Targeting of Antisense Oligodeoxynucleotides to Ovarian Cancer Cells" Pharm. Res. 15:1540-1545 (1998).
Lipson et al., "Psoralen cross-linking of ribosomal RNA" *Methods in Enzymology* 164:330-341 (1988).
Liu et al., "Detection of a novel ATP-dependent cross-linked protein at the 5' splice site-U1 small nuclear RNA duplex by methylene blue-mediated photo-cross-linking" *Mol. Cell Biol.* 18:6910-6920 (1998).
Livache et al., "Detection of HIV1 DNA in Biological Samples by an Homogenous Assay: Fluorescence Measurement of Double-Stranded RNA Synthesized from Amplified DNA" Analytical Biochemistry 217:248-254 (1994).
Luo et al., "The Gene-Silencing Efficiency of SiRNA is Strongly Dependent on the Local Structure of mRNA at the Targeted Region" Biochemical and Biophysical Research Communications 318:303-10 (2004).
Maitra et al., "HIV-1 TAR RNA Has an Intrinsic Ability to Activate Interferon-Inducible Enzymes" Virology 204:823-827 (1994).
Manoharan, "Oligonucleotide Conjugates as Potential Antisense Drugs with Improved Uptake, Biodistribution, Targeted Delivery and Mechanism of Action" Antisense and Nucleic Acid Drug Development 12:103-128 (2002).
Manoharan et al., "Chemical Modifications to Improve Uptake and Bioavailability of Antisense Oligonucleotides" Ann. NY Acad. Sci. 660:306-309 (1992).
Manoharan et al., "Introduction of a Lipophilic Thioether Tether in the Minor Groove of Nucleic Acids for Antisense Applications" Bioorg. Med. Chem. Lett. 3:2765-2770 (1993).
Manoharan et al., "Cholic Acid-Oligonucleotide Conjugates for Antisense Applications" Bioorg. Med. Chem. Lett. 4:1053-1060 (1994).
Manoharan et al., "Oligonucleotide Conjugates Alteration of the Pharmacokinetic Properties of Antisense Agents" Nucleosides & Nucleotides 14:969-973 (1995).
Manoharan et al., "Lipidic Nucleic Acids" Tetrahedron 36:3651-3654 (1995).
Marques et al., "A Structural Basis for Discriminating Between Self and Non-Self Double-Stranded RNAs in Mammalian Cells" Nature Biotechnology 24:559-65 (2006).
Maru, "Molecular Biology of Chronic Myeloid Leukemia" Int. J. Hematol. 73:308-322 (2001).
Matrisian, "Cancer biology: Extracellular proteinases in malignancy" Curr. Biol. 9:R776-778 (1999).
Meister, "RNA Interference in the Nucleus" Science 321:496-497, 2008.
Mendelsohn et al., "The EGF receptor family as target for cancer therapy" Oncogene 19:6550-6565 (2000).
Micura et al., "Cyclic oligoribonucleotides (RNA) by soli-phase synthesis" *Chem. Eur. J.* 5:2077-2082 (1999).
Mignatti et al., "Biology and Biochemistry of proteinases in Tumor Invasion" Physiol. Rev. 73:161-195 (1993).
Milligan et al., "Synthesis of Small RNAs Using T7 RNA Polymerase" Methods in Enzymology 180:51-62 (1989).
Mishra et al., "Improved leishmanicidal effect of phosphorotioate antisense oligonucleotides by LDL-mediated delivery" Biochem. Biophys. Acta. 264:229-237 (1995).
Mizuno et al., "Regulation of Gene Expression by a Small RNA Transcript (micRNA) in *Escherichia coli* K-12)" Proc. Japan Acad. 59:335-338 (1983).
Mullauer et al., "Mutations in apoptosis genes: a pathogenetic factor for human disease" Mutat. Res. 488:211-231 (2001).
Muzyczka, "Use of Adeno-Associated Virus as a General Transduction Vector for Mammalian Cells" Curr. Topics Micro. Immunol. 158:97-129 (1992).

Napoli et al., "Introduction of a chimeric Chalcone Synthase Gene into Petunia Results in Reversible Co-Suppression of Homologous Genes in trans" The Plant Cell 2:279-289 (1990).
Normanno et al., "The role of EGF-Related Peptides in Tumor Growth" Front. Biosci. 6:D685-707 (2001).
Novina et al., "The RNAi revolution" Nature Publishing Group 430:161-164 (2004).
Oates et al., "Too Much Interference: Injection of Double-Stranded RNA Has Non-Specific Effects in the Zebrafish Embryo" Developmental Biology 24:20-28 (2000).
Oberhauser et al., "Effective incorporation of 2'-O-methyl-oligoribonucleotides into liposomes and enhanced cell association through modification with thiocholesterol" Nucl. Acids Res. 20:533-538 (1992).
Obika et al., "Stability and structural features of the duplexes containing nucleoside analogues with a fixed N-type conformation, 2'-O, 4'-C-mehtyleneribonucleosides" Tetrahedron 39:5401-5404 (1998).
Opalinska et al., "Nucleic acid therapeutics: basic principles and recent applications" Nature Review 11:503-514 (2002).
Ouchi et al., "Synthesis and Antitumor Activity of Poly(Ethylene Glycol)s Linked to 5-Flurouracil via Urethane or Urea Bond" Drug Design and Discovery 9:93-105 (1992).
Oxford Advanced Learner's Dictionary of Current English, p. 253.
Pandolfi, "In vivo analysis of the molecular genetics of acute promyelocytic leukemia"Oncogene 20:5726-5735 (2001).
Parrish et al., Functional Anatomy of a dsRNA Trigger: Differential Requirement for the Two Trigger Strands in RNA Interference, Molecular Cell 6:1077-1087 (2000).
Paroo et al., "Challenges for RNAi in vivo" Trends in Biotech. 22(8):390-394 (2004) Elsevier.
Paul et al., "Effective expression of small interfering RNA in human cells" Nature Biotech. 29:505-508 (2002).
Pei et al., "On the Art of Identifying Effective and Specific siRNAs" Nature Methods 3: 670-676 (2006).
Phillips et al., "The NZB Mouse as a Model for Chronic Lymphocyte Leukemia" Cancer Res. 52:437-443 (2000).
Pils et al., "Flexible non-nucleotide linkers as loop replacements in short double helical RNAs," Nucleic Acids Research 28:1869-1963 (2000).
Pollock et al., "Mouse models of acute promyelocytic leukemia" Curr. Opin. Hematol. 8:206-211 (2001).
Polushin et al., "Synthesis of Oligonucleotides Containing 2'-Azido- and 2'-Amnio-2'deoxyuridine Using Phosphtriester Chemistry" Tetrahedron 37:3227-3230 (1996).
Prakash et al., "Positional effect of chemical modifications on short interference RNA activity in mammalian cells" J. Med. Chem. 48:4247-4253 (2005).
Pschyrembel Klinisches Worterbuch, 259, neu bearbeitete Auflage (2002).
Pusch et al., "Nucleotide Sequence Homology Requirements of HIV-1 Specific Short Hairpin RNA" Nucleic Acids Research 31:6444-6449 (2003).
Ravasio, "Selective Hydrogenations Promoted by Copper Catalysts. I. Chemoselectivity, Regioselectivity, and Stereoselectivity in the Hydrogenation of 3-Substituted Steroids" J. Org. Chem. 56:4329-4333 (1991).
Reed, "Mechanisms of Apoptosis" Am. J. Pathol. 157:1415-1430 (2000).
Rego et al., "Analysis of the Molecular Genetics of Acute Promyelocytic Leukemia in Mouse Models" Semin. in Hemat. 38:54-70 (2001).
Reynolds et al., "Rational siRNA design for RNA interference" Nature Biotechnology 22:326-330 (2004).
Rosenfeld et al., "Adenovirus-Mediated Transfer of a Recombinant a-Antitrypsin Gene to the Lung Epithelium in vivo" Science 252:431-434 (1991).
Rosenfeld et al., "In vivo Transfer to the Human Cystic Fibrosis Transmembrane Conductance Regulator Gene to the Airway Epithelium" Cell 68:143-155 (1992).
Saison-Behmoaras et al., "Short modified antisense oligonucleotdies directed against Ha-ras point mutation induce selective cleavage of the mRNA and inhibit T24 cells proliferation" EMBO J. 10:111-118 (1991).

Scheffer et al., "The drug resistance-related protein LRP is the human major vault protein" Nat. Med. 1:578-582 (1995).
Scherr et al., "Quantitative Determination of Lentiviral Vector Particle Numbers by Real-time PCR" BioTechniques 31:520-526 (2001).
Schwarz et al., "Asymmetry in the assembly of the RNAi complex" Cell 115:199-208 (2003).
Schwarz et al., "Evidence that siRNAs function as guides not primers in the Drosophila and human RNAi pathways," Mol. Cell. 10:537-48 (2002).
Schlingensiepen et al., Antisense—From Technology to Therapy. Blackwell Science Ltd., vol. 6 (1997).
Secrist et al., Abstract 21, Program & Abstracts, Tenth International Roundtable, Nucleosides, Nucleotides and their Biological Applications, Park City, Utah, Sep. 16-20, 1992.
Shannon et al., "Modelling myeloid leukemia tumors suppressor gene inactivation in the mouse" Semin. Cancer Biol. 1:191-199 (2001).
Shea et al., "Synthesis, hybridization properties and antiviral activity of lipid-oligodeoxynucleotide conjugates" Nucl. Acids Res. 18:3777-3783 (1990).
Sharp, "RNA Interference-2001," Genes and Development 15:485-490 (2001).
Sijen et al., "On the Role of RNA Amplification in dsRNA-Triggered Gene Silencing," Cell 107:465-476 (2001).
Simons et al., "Translational Control of IS10 Transposition" Cell 34:683-691 (1983).
Skorski et al., "Suppression of Philadelphia Leukemia cell growth in mice by BCR-ABL antisense oligodeoxynucleotide" Proc. Natl. Acad. Sci. USA 91:4504-4508 (1994).
Sledz et al., "RNA Interference and Double-Stranded RNA Activated Pathways" Biochemical Society Transactions 32:956-956 (2004).
Stetler-Stevenson et al., "Tumor Cell Interactions with the Extracellular Matrix During Invasion and Metastasis" Annu. Rev. Cell Biol. 9:541-573 (1993).
Strasser et al., "Apoptosis Signaling" Annu. Rev. Biochem. 69:217-245 (2000).
Svinarchuk et al., "Inhibition of HIV proliferation in MT-4 cells by antisense oligonucleotie conjugated to lipophilic groups" Biochimie 75:49-54 (1993).
Takayama et al., "Antisense RNA" Critical Reviews in Biochemistry and Molecular Biology 25:155-184 (1991).
Thomson et al., "Synthesis and Properties of Diuridine Phosphate Analogues Containing Thio and Amino Modifications" J. Org.Chem. 61:6273-6281 (1996).
Thomson et al., "Activity of hammerhead ribozymes containing non-nucleotide linkers" Nucl. Acids Res. 21:5600-5603 (1993).
Tolun et al., "Direct Repeats of the F Plasmid incC Region Express F Incompatibility" Cell 24: 687-694 (1981).
Tsutsui et al., "Role of Nine Repeating Sequences of the Mini-F Genome for Expression of F-Specific Incompatibility Phenotype and Copy Number Control" Journal of Bacteriology 155:337-344 (1983).
Uhlenbeck, "A Small Catalytic Oligoribonucleotide" Nature 328:596-600 (1987).
U.S. Appl. No. 60/175,440, filed Jan. 11, 2000.
Van Beusechem et al., "Long-term expression of human adenosine deaminase in rhesus monkeys transplanted with retrovirus-infected bone-marrow cells" Proc. Natl. Acad. Sci. USA 89:7640-7644 (1992).
Van Etten, "Pathogenesis and treatment of Ph leukemia: recent insights from mouse models" Curr. Opin. Hematol. 8:224-230 (2001).
Various, "Nature Insight: RNA Interference" Nature, 431:337-378 (2004) (Table of Contents).
Verma et al., "Human gene therapy" Nature 389:239-242 (1997).
Vickers et al., "Efficient Reduction of Target RNAs by Small Interfering RNA and RNase H-dependent Antisense Agents. A Comparative Analysis" J. Biol. Chem. 278:7108-7118 (2003).
Wacheck et al., "Small Interfering RNA Targeting Bcl-2 Sensitizers Malignant Melanoma" Oligonucleotides 13:393-400 (2003).
Wagner, "The state of the art in antisense research" Nat. Med. 1:1116-1118 (1995).

Wang et al., "Circular RNA oligonucleotides. Synthesis, nucleic acid binding properties, and a comparison with circular DNAs" Nucl. Acids Res. 22:2326-2333 (1994).
Wang et al., "RNA conformation in the Tat-TAR complex determined by site-specific photo-cross-linking" Biochem 35:6491-6499 (1996).
Watkins et al., "In vivo UV cross-linking of U snRNAs that participate in trypanosome trans-splicing" Genes & Development 5:1859-1869 (1991).
Wengel, "Synthesis of 3'-C- and 4'-C-branched oligodeoxynucleotides and the development of locked nucleic acid (LNA)" Acc. Chem. Res. 32:301-310 (1999).
Williams et al., "Thermodynamic Comparison of the Salt Dependence of Natural RNA Hairpins and RNA Hairpins with Non-Nucleotide Spacers" Biochemistry 35:14665-14670 (1996).
Wilson et al., "Retrovirus-mediated transduction of adult hepatocytes" Proc. Natl. Acad. Sci. USA 85:3014-3018 (1998).
Wink, Molekulare Biotechnologie, Wiley-VCH 557-577 (2004).
Wong et al., "Modeling Philadelphia chromosome positive leukemias" Oncogene 20:5644-5659 (2001).
Yokota, "Tumor progression and metastasis" Carcinogenesis 21:497-503 (2000).
Zeng et al., "The Fetal Origin of B-Precursor Leukemia in the Eu-ret Mouse" Blood 92:3529-3536 (1998).
Zhang et al., "Single processing center models for human dicer and bacterial RNase III" Cell 118:57-68 (2004).
Zhang et al., "Targeted Gene Silencing by Small Interfering RNA-based Knock-Down Technology" Current Pharma. Biotech 5:1-7 (2004).
Zwieb et al., "Evidence for RNA-RNA cross-link formation in Escherichia coli ribosomes" Nucl. Acids Res. 5:2705-2720 (1978).
Statement of Grounds and Particulars of Opposition to Australian Patent Application No. 2005201044, filed by Sirna Therapeutics (Dec. 1, 2008).
Lederer & Keller: German Opposition, filed by Pfizer Inc. on Jun. 19, 2008, in opposition to German Patent DE 100 66 235.8 (translation attached).
Decision of Board of Appeal in Opposition for EP 1144623 (Mar. 29, 2009) (translation attached).
Decision Revoking Patent and Grounds for Decision in Opposition proceedings for EP 1214945 (Mar. 31, 2009).
Nakamura et al., "How Does RNase H recognize a DNA-RNA Hybrid?" Proc. Natl. Acad. Sci. 88:11535-11539 (1991).
Decision in opposition proceedings for European Patent No. 11 44 623 (Mar. 30, 2009). (translation attached).
Decision and Minutes in opposition proceedings for European Patent No. 12 14 945 (Mar. 31, 2009). (translation attached).
Record for the Oral proceedings before the Opposition Division from European Patent Office, in opposition of European Patent No. 1214945, Mar. 31, 2009, 92 Pages.
Grounds of Appeal filed by Alnylam Europe AG for European Patent EP 1214945, filed Aug. 5, 2009, 21 pages.
Minutes of oral proceedings for European Patent EP 1214945, May 19, 2010, 13 pages.
Response to patentee's Grounds of Appeal filed by Quark Biotech, Inc. for European Patent EP 1214945, filed Dec. 28, 2009, 12 pages.
Response to Preliminary Opinion of the Board of Appeal for European Patent EP 1214945, filed by Sirna Therapeutics, Inc., filed on Apr. 16, 2010, 10 pages.
Response to patentee's Grounds of Appeal filed by Sirna Therapeutics AG for European Patent EP 1214945, filed Dec. 23, 2009, 60 pages.
Summons to Attend Oral Hearing regarding opposition against European Patent EP 1214945, Feb. 26, 2010, 15 Pages.
Decision of the Technical Board of Appeals for European Patent No. 1144623, Dec. 9, 2008, 50 Pages.
Response to Summons for oral proceedings in Opposition against EP 1214945 filed by Silence Therapeutics AG, filed on Apr. 19, 2010, 5 pages.
Response to Summons to Attend Oral proceedings issued by the German Patent and Trademark office on Dec. 9, 2009 regarding opposition against German Patent DE 10066235.8, filed by Alnylam Europe AG and Jan. 4, 2010, 36 Pages.

Minutes of oral proceedings regarding opposition against German Patent DE 10066235.8, Feb. 5, 2010, 14 Pages.
Notice of Acceptance for Australian patent application No. AU 2008202208, Oct. 19, 2009, 3 pages.
Notice of Opposition to Australian patent application No. AU 2008202208 filed by Sirna Therapeutics, Inc., filed on Jan. 29, 2010, 1 page.
Statement of Grounds & Particulars of Opposition to Australian patent application No. AU 2008202208 filed by Sirna Therapeutics, Inc., filed on Apr. 29, 2010, 28 pages.
Notice of Opposition to European Patent EP 1550719 filed by Sarah Elizabeth Rogues, filed Sep. 23, 2009, 24 pages.
Notice of Opposition to European Patent EP 1550719 filed by Sanofi-Aventis Deutschland GmbH, filed Sep. 23, 2009, 46 pages.
Notice of Opposition to European Patent EP 1550719 filed by Pfizer Limited, filed Sep. 23, 2009, 21 pages.
Notice of Opposition to European Patent EP 1550719 filed by Silence Therapeutics AG, filed Sep. 24, 2009, 35 pages.
Response to Notice of Opposition to European Patent EP 1550719 filed by Alnylam Europe AG, filed Mar. 15, 2010, 40 pages.
Response to Notice of Opposition filed against German Patent No. DE 01985833, filed by Max-Plank—Gesellschaft zur Forderung der Wissenschaften e.V., Mar. 26, 2009, 4 pages.
Petition regarding German Patent No. DE 10080167 filed by Silence Therapeutics AG, Mar. 17, 2009, 9 Pages.
Minutes of the Oral Proceedings held on Jan. 14, 2010 in Opposition to German Patent DE 10066235.8, issued by the German Patent and Trademark Office, 55 Pages.
Decision of the Board of Appeal of May 19, 2010 in Opposition to European Patent No. EP 1214945, Jul. 20, 2010, 28 pages.
Statutory Declaration by David Keith Myers dated Aug. 2, 2010, filed by Sirna Therapeutics, Inc., in opposition to Australia Patent No. AU 778474, 3 pages.
Statutory Declaration by David Keith Myers dated Nov. 7, 2008, filed by Sirna Therapeutics, Inc., in opposition to Australia Patent No. AU 778474, 16 pages, list of journals published before the end of 1999 which cite a journal article authored by Andrew Fire and co-workers, and published in the journal Nature on Feb. 19, 1998.
Statutory Declaration by David Keith Myers dated Nov. 7, 2008, filed by Sirna Therapeutics, Inc., in opposition to Australia Patent No. AU 778474, 3 pages, list of patent publications having an earliest claimed priority date of Nov. 24, 1999 or earlier, which cite Fire, A., et al., (1998), Potent and specific genetic interference by double-stranded RNA in Caenorhabditis elegans, Nature 391: 806-811.
Submission by Alnylam Europe in opposition proceedings for European Patent No. 1144623 (Dec. 7, 2004), 140 pages.
Submission by Alnylam Europe in opposition proceedings for European Patent No. 1144623 (Apr. 21, 2006), 63 pages.
Grounds of Appeal filed by Appellant Silence Therapeutics AG, on Nov. 23, 2010, against German Patent No. DE 10066235.8, 49 pages.
Grounds of Appeal filed by Appellant Sanofi-Aventis Deutschland GmbH, on Oct. 26, 2010, against German Patent No. DE 10066235.8, 21 pages.
Office Action for U.S. Appl. No. 11/982,305, Feb. 11, 2011, 13 pages.
Office Action for U.S. Appl. No. 11/982,305, Sep. 3, 2010, 10 pages.
Office Action for U.S. Appl. No. 11/982,425, Feb. 11, 2011, 13 pages.
Office Action for U.S. Appl. No. 11/982,425, Sep. 2, 2010, 10 pages.
Office Action for U.S. Appl. No. 10/382,768, Nov. 26, 2010, 7 pages.
Office Action for U.S. Appl. No. 11/982,345, Oct. 6, 2010, 11 pages.
Office Action for U.S. Appl. No. 11/982,434, Oct. 6, 2010, 11 pages.
Office Action for U.S. Appl. No. 11/982,325, Oct. 6, 2010, 11 pages.
Office Action for U.S. Appl. No. 10/383,099, Oct. 15, 2010, 19 pages.
Office Action for U.S. Appl. No. 10/612,179, Oct. 20, 2010, 24 pages.
Agrawal, S., et al., "Protocols for Oligonucleotides and Analogs," Chapters 5 and 6, 1993, pp. 81-140, Humana Press, Totowa, NH.
Baxevanis, A., "The Molecular Biology Database Collection: 2003 udpate," Nucleic Acids Research, 2003, pp. 1-12, vol. 31, No. 1.
Bernstien, E., et al., "Role for a bidentate ribonuclease in the initation step of RNA interference," Nature, Jan. 18, 2001, pp. 363-366, vol. 409.
Braun, H., et al., "Oligonucleotide and plasmid DNA packaging into polyoma VPI virus-like particles expressed in *Escherichia coli*," Biotechnol. Appl. Biochem., 1999, pp. 31-43.
Biotechnology Applied Biochemistry vol. 29, Part 1, Feb. 1999, which shows Braun, H., et al., "Oligonucleotide and plasmid DNA packaging into polyoma VPI virus-like particles expressed in *Escherichia coli*," as first published on the internet Dec. 22, 1998.
Chen, M., et al., "A universal plasmid library encoding all permutations of small interfering RNA," PNAS, Feb. 15, 2005, pp. 2356-2361, vol. 102, No. 7.
Chu, C-Y., et al., "Potent RNAi by short RNA triggers," RNA, Report, 2008, pp. 1714-1719, vol. 14.
Clemens, M.J., "PKR—a protein kinase regulated by double-stranded RNA," Int J Biochem Cell Biol., 1997, 29(7):945-949.
Crooke, S., et al., "Antisense Research and Applications," Chapters 16 and 18, 1993, CRC Press, Boca Raton, 21 pages.
Fire, A., "Gene Silencing by Double Stranded RNA," Nobel Lecture, Dec. 8, 2006, pp. 198-233.
Gewritz, A., et al., "Nucleic Acid Therapeutics: State of the Art and Future Prospects," Blood, Aug. 1, 1998, pp. 712-736, vol. 92, No. 3.
Hung, C., et al., "A novel siRNA validation system for functional screening and identification of effective RNAi probes in mammalian cells," Biochemical and Biophysical Research Communications, 2006, pp. 707-720, vol. 346.
Morita, T., et al., "RNAi Provides a New Tool for Functional Analyses of Mammalian Genes", Proteins, Nucleic Acids and Enzymes, vol. 47, No. 14, 2002, pp. 1939-1945, with English Abstract.
Overview, Arthritis Research & Therapy: http://arthritis-research.com/content/figures/ar1168-1.jpg, Jan. 12, 2010.
Phillips, M., "Antisense Inhibition and Adeno-Associated Viral Vector Delivery for Reducing Hypertension," Hypertension, Journal of the American Heart Association, 1997, pp. 177-187, vol. 29.
Pschyrembel Klinisches Worterbuch, 259., neu bearbeitete Auflage, Pschyrembel Clinical Dictionary $259^{th}$, Revised Edition, 2002, 1 page, with English summary.
Rumney, S., et al., "Structural Optimization of Non-Nucleotide Loop Replacements for Duplex and Triplex DNAs," J. Am. Chem. Soc., 1995, pp. 5635-5646, vol. 117.
Shiota et al., "I want to Know the RNAi Protocol of that Animal!—Effective RNAi in Mammal Cells", Cell Engineering, vol. 22, No. 3, 2003, pp. 310-315, with English summary.
Stryer, L., Biochemistry, Part 1 Molecular Design of Life, Chapter 4 DNA and RNA: Molecules of Heredity, 1988, pp. 80-82.
Sui, G., et al., "A DNA vector-based RNAi technology to suppress gene expression in mammalian cells," Proc. Natl. Acad. Sci. USA, Apr. 16, 2002, pp. 5515-5520, vol. 99, No. 8.
Wang, S., et al., "Delivery of antisense oligodeoxyribonucleotides against the human epidermal growth factor receptor into cultured KB cells with liposomes conjugated to folate via polyethylene glycol," Proc. Nat. Acad. Sci., Biochemistry, Apr. 1995, pp. 3318-3322.
Wang et al., "RNA conformation in the Tat-TAR complex determined by site-specific photo-cross-linking," Biochem 35:6491:6499 (1996).
Zelphati, O., et al., "Antisense oligonucleotides in solution of encapsulated in immunoliposomes inhibit replication of HIV-1 by several different mechanisms," Nucleic Acids Research, 1994, pp. 4307-4314, vol. 22, No. 20.
Zheng, L., et al., "An approach to genomewide screens of expressed small interfering RNAs in mammalian cells," Proc. Natl. Acad. Sci. USA, Jan. 6, 2004, pp. 135-140, vol. 101, No. 1.
Examination Report for German Divisional Patent Application No. DE 10066382.6, Apr. 8, 2011, 13 pages.
Office Action for U.S. Appl. No. 11/982,325, Mar. 18, 2011, 12 pages.
Office Action for U.S. Appl. No. 11/982,345, Mar. 18, 2011, 14 pages.
Office Action for U.S. Appl. No. 11/982,434, Mar. 18, 2011, 12 pages.
Office Action for U.S. Appl. No. 10/383,099, Mar. 30, 2011, 10 pages.
Extended European Search Report and Written Opinion, mailed Aug. 8, 2011 for European Patent Application No. EP 10011217.6, 21 Pages.
Statement of Grounds & Particulars of Opposition filed by Sirna Therapeutics, Inc., on Aug. 23, 2011, for Australian Patent Application No. AU 778474, 9 pages.

Statutory Declaration dated Aug. 17, 2010 by David M. Stalker with Exhibits DMS-A to DMS-C and Exhibits DMS-41 to DMS-74 thereto in respect of opposition to accepted Australian Patent Application No. 2005201044, 30 pages.

Office Action dated Aug. 26, 2011, for U.S. Appl. No. 10/383,099, 5 pages.

Current version of Curriculum Vitae of David M. Stalker, 2010, 13 pages.

Agrawal, S., "Antisense oligonucleotides: towards clinical trials," Tibtech (1996), 14: 376-387.

Agrawal, S., et al., "Oligodeoxynucleoside phosphoramidates and phosphorothioates as inhibitors of human immunodeficiency virus," Proc. Natl. Acad. Sci. USA (1988), 85:7079-7083.

Baulcombe, D.C., et al., "Mechanisms of Pathogen-Derived Resistance to Viruses in Transgenic Plants," The Plant Cell (1996), 8: 1833-1844.

Bumcrot, D., et al., "RNAi therapeutics: a potential new class of pharmaceutical drugs," Nature Chemical Biology (2006), 2(12): 711-719.

Corey, D.R., "Chemical modification: the key to clinical application of RNA interference?" The Journal of Clinical Investigation (2007), 117(12): 3615-3622.

Dean, N.M., et al., "Identification and Characterization of Second-Generation Antisense Oligonucleotides," Antisense & Nucleic Acid Drug Development (1997), 7: 229-233.

Forstova, J. et al., "Polyoma Virus Pseudocapsids as Efficient Carriers of Heterologous DNA into Mammalian Cells," Human Gene Therapy (1995), 6: 297-306.

Gamier, L. et al., "Incorporation of Pseudorabies Virus gD into Human Immunodeficiency Virus Type 1 Gag Particles Produced in Baculovirus-Infected Cells," Journal of Virology (1995) 69(7): 4060-4068.

Gillock, E. T. et al., "Polyomavirus Major Capsid Protein VP1 is Capable of Packaging Cellular DNA When Expressed in the Baculovius System," Journal of Virology (1997),71(4): 2857-2865.

Hamada M. et al., "Effects of RNA Interference in Gene Expression (RNAi) in Cultured Mammalian Cells of Mismatches and the Introduction of Chemical Modifications at the 3'-Ends of siRNAs," Antisense and Nucleic Acid Drug Development, 2002, vol. 12, pp. 301-309.

Judge A.D., et al., "Design of Noninflammatory Synthetic siRNA Mediating Potent Gene Silencing in Vivo," Molecular Therapy (2006), 13(3): 494-505.

Kelly, J. "Superagonist Trial Hit by Cytokine Storm," Muscoskeletal Report, Aug. 17, 2006, 3 Pages.

Lamond, A., et al., "Antisense oligonucleotides made of 2'-O-alkylRNA: their properties and applications in RNA biochemistry," FEBS Letters (1993), 325(1-2): 123-127.

Lopez-Fraga, M., et al., "RNA Interference-Based Therapeutics: New Strategies to Fight Infectious Disease," Infectious Disorders Drug Targets (2008), 8:262-273.

Manoharan, M., "RNA interference and chemically modified small interfering RNAs," Current Opinion in Chemical Biology (2004), 8: 570-579.

Monia, B.P. et al., "Evaluation of 2'-Modified Oligonucleotides Containing 2'-Deoxy Gaps as Antisense Inhibitors of Gene Expression," The Journal of Biological Chemistry (1993), 268(19): 14514-14522.

Malone, R.W. et al., "Cationic liposome-mediated RNA transfection," Proc. Natl. Acad. Sci. USA (1989), 86: 6077-6081.

Sedlik, C. et al., "Recombinant parvovirus-like particles as an antigen carrier: A novel nonreplicative exogenous antigen to elicit protective antiviral cytotoxic T cells," Proc. Natl. Acad. Sci. USA (1997) 94: 7503-7508.

Seow, Y., et al., "Biological Gene Delivery Vehicles: Beyond Viral Vectors," Molecular Therapy (2009), 17(5): 767-777.

Soeda, E., et al., "Enhancement by polylysine of transient, but not stable, expression of genes carried into cells by polyoma VP1 pseudocapsids," Gene Therapy (1998), 5: 1410-1419.

Sporlein, B., et al., "Lipofectin: direct gene transfer to higher plants using cationic liposomes," Theoretical and Applied Genetics (1991), 83: 1-5.

Suntharalingam, G., et al., "Cytokine Storm in a Phase 1 Trial of the Anti-CD28 Monoclonal Antibody TGN1412," New England Journal of Medicine (2006), 355(10): 1018-1028.

Touze, A., et al., "In vitro gene transfer using human papillomavirus-like particles," Nucleic Acids Res. (1998) 26(5): 1317-1323.

Zamecnik, P.C., et al., "Inhibition of Rous sarcoma virus replication and cell transformation by a specific oligodeoxynucleotide," Proc. Natl. Acad. Sci. USA (1978), 75(1): 280-284.

Office Action Communication by the German Patent and Trademark Office dated Apr. 11, 2011 for German Divisional Patent Application No. 10066344.3-41, 7 pages.

Office Action Communication pursuant to Article 94(3) EPC dated Jul. 8, 2011, for European Patent Application No. EP 06025389.5, 8 pages.

Official Inquiry dated May 17, 2011, for Japanese Patent Application No. 2007-186341 (Appeal No. 2009-11871), 6 pages.

Official Inquiry dated May 17, 2011, for Japanese Patent Application No. 2007-186340 (Appeal No. 2009-11715), 11 pages.

Official Inquiry dated May 17, 2011, for Japanese Patent Application No. 2007-186339 (Appeal No. 2009-11870), 10 pages.

Office Action dated Jun. 17, 2011, for U.S. Appl. No. 10/612,179, 11 Pages.

Sen, G., et al., "*A Brief History of RNAi: The Silence of the Genes*," FASEB J., vol. 20, pp. 1293-1299, 2006.

Request that patent be revoked in its entirety, in Opposition against European Patent 1214945, filed with European Patent Office Opposition Division, filed by Opponent 1, SIRNA Therapeutics on Aug. 16, 2011, 49 Pages.

Response to the Submission of Opponent 1, filed by Alnylam Europe AG on Nov. 17, 2011, Opposition against European Patent EP 1550719, 17 Pages.

Reply to Office Action per article 94 (3) EPC of Jul. 8, 2011, filed on Nov. 17, 2011, European Patent Application No. EP 06025389.5, 5 pages.

Written Reply filed on Oct. 17, 2011, Japanese Patent Application No. JP 2007-186341, 70 pages.

Written Reply filed on Oct. 17, 2011, Japanese Patent Application No. JP 2007-186340, 76 pages.

Written Reply filed on Oct. 17, 2011, Japanese Patent Application No. JP 2007-186339, 77 pages.

Notice of Reasons for Rejection, mailed on Nov. 1, 2011, Japanese Patent Application No. JP 2009-002825, 9 Pages.

Summons to attend oral proceedings pursuant to Rule 115(1) EPC issued by the European Patent Office on Nov. 25, 2011, for Opposition against European Patent No. EP 1550719, 50 Pages.

* cited by examiner

METHOD AND MEDICAMENT FOR INHIBITING THE EXPRESSION OF A GIVEN GENE

CROSS REFERENCE TO RELATED APPLICATIONS

This application is a continuation of U.S. patent application Ser. No. 10/612,179, filed Jul. 2, 2003, which is a divisional of U.S. patent application Ser. No. 09/889,802, filed Sep. 17, 2001, now abandoned, which is the National Stage of International Patent Application No. PCT/DE00/00244, filed Jan. 29, 2000, which claims priority to German Patent Application No. DE19903713.2, filed Jan. 30, 1999, and German Patent Application No. DE19956568.6, filed Nov. 24, 1999. The contents of these prior applications are hereby incorporated by reference in their entirety for all purposes.

The invention relates to methods in accordance with the preambles of claims 1 and 2. It furthermore relates to a medicament and to a use of double-stranded oligoribonucleotides and to a vector encoding them.

Such a method is known from WO 99/32619, which was unpublished at the priority date of the present invention. The known process aims at inhibiting the expression of genes in cells of invertebrates. To this end, the double-stranded oligoribonucleotide must exhibit a sequence which is identical with the target gene and which has a length of at least 50 bases. To achieve efficient inhibition, the identical sequence must be 300 to 1 000 base pairs in length. Such an oligoribonucleotide is complicated to prepare.

DE 196 31 919 C2 describes an antisense RNA with specific secondary structures, the antisense RNA being present in the form of a vector encoding it. The antisense RNA takes the form of an RNA molecule which is complementary to regions of the mRNA. Inhibition of the gene expression is caused by binding to these regions. This inhibition can be employed in particular for the diagnosis and/or therapy of diseases, for example tumor diseases or viral infections. —The disadvantage is that the antisense RNA must be introduced into the cell in an amount which is at least as high as the amount of the mRNA. The known antisense methods are not particularly effective.

U.S. Pat. No. 5,712,257 discloses a medicament comprising mismatched double-stranded RNA (dsRNA) and bioactive mismatched fragments of dsRNA in the form of a ternary complex together with a surfactant. The dsRNA used for this purpose consists of synthetic nucleic acid single strands without defined base sequence. The single strands undergo irregular base pairing, also known as "non-Watson-Crick" base pairing, giving rise to mismatched double strands. The known dsRNA is used to inhibit the amplification of retroviruses such as HIV. Amplification of the virus can be inhibited when non-sequence-specific dsRNA is introduced into the cells. This leads to the induction of interferon, which is intended to inhibit viral amplification. The inhibitory effect, or the activity, of this method is poor.

It is known from Fire, A. et al., NATURE, Vol. 391, pp. 806 that dsRNA whose one strand is complementary in segments to a nematode gene to be inhibited inhibits the expression of this gene highly efficiently. It is believed that the particular activity of the dsRNA used in nematode cells is not due to the antisense principle but possibly on catalytic properties of the dsRNA, or enzymes induced by it. —Nothing is mentioned in this paper on the activity of specific dsRNA with regard to inhibiting the gene expression, in particular in mammalian and human cells.

The object of the present invention is to do away with the disadvantages of the prior art. In particular, it is intended to provide as effective as possible a method, medicament or use for the preparation of a medicament, which method, medicament or use is capable of causing particularly effective inhibition of the expression of a given target gene.

This object is achieved by the features of the claims presented below. Advantageous embodiments can be seen from these claims.

In accordance with the method oriented inventions, it is provided in each case that the region I which is complementary to the target gene exhibits not more than 49 successive nucleotide pairs.

Provided in accordance with the invention are an oligoribonucleotide or a vector encoding therefor. At least segments of the oligoribonucleotide exhibit a defined nucleotide sequence. The defined segment may be limited to the complementary region I. However, it is also possible that all of the double-stranded oligoribonucleotide exhibits a defined nucleotide sequence.

Surprisingly, it has emerged that an effective inhibition of the expression of the target gene can be achieved even when the complementary region I is not more than 49 base pairs in length. The procedure of providing such oligoribonucleotides is less complicated.

In particular, dsRNA with a length of over 50 nucleotide pairs induces certain cellular mechanisms, for example the dsRNA-dependent protein kinase or the 2-5A system, in mammalian and human cells. This leads to the disappearance of the interference effect mediated by the dsRNA which exhibits a defined sequence. As a consequence, protein biosynthesis in the cell is blocked. The present invention overcomes this disadvantage in particular.

Furthermore, the uptake of dsRNA with short chain lengths into the cell or into the nucleus is facilitated markedly over longer-chain dsRNAs.

It has proved advantageous for the dsRNA or the vector to be present packaged into micellar structures, preferably in liposomes. The dsRNA or the vector can likewise be enclosed in viral natural capsids or in chemically or enzymatically produced artificial capsids or structures derived therefrom. —The abovementioned features make it possible to introduce the dsRNA or the vector into given target cells.

In a further aspect, the dsRNA has 10 to 1 000, preferably 15 to 49, base pairs. Thus, the dsRNA can be longer than the region I, which is complementary to the target gene. The complementary region I can be located at the terminus or inserted into the dsRNA. Such dsRNA or a vector provided for coding the same can be produced synthetically or enzymatically by customary methods.

The gene to be inhibited is expediently expressed in eukaryotic cells. The target gene can be selected from the following group: oncogene, cytokine gene, Id protein gene, developmental gene, prion gene. It can also be expressed in pathogenic organisms, preferably in plasmodia. It can be part of a virus or viroid which is preferably pathogenic to humans. —The method proposed makes it possible to produce compositions for the therapy of genetically determined diseases, for example cancer, viral diseases or Alzheimer's disease.

The virus or viroid can also be a virus or viroid which is pathogenic to animals or plant-pathogenic. In this case, the method according to the invention also permits the provision of compositions for treating animal or plant diseases.

In a further aspect, segments of the dsRNA are designed as double-stranded. A region II which is complementary within the double-stranded structure is formed by two separate RNA single strands or by autocomplementary regions of a topologically closed RNA single strand which is preferably in circular form.

The ends of the dsRNA can be modified to counteract degradation in the cell or dissociation into the single strands. Dissociation takes place in particular when low concentrations or short chain lengths are used. To inhibit dissociation in a particularly effective fashion, the cohesion of the complementary region II, which is caused by the nucleotide pairs, can be increased by at least one, preferably two, further chemical linkage(s). —A dsRNA according to the invention whose dissociation is reduced exhibits greater stability to enzymatic and chemical degradation in the cell or in the organism.

The complementary region II can be formed by autocomplementary regions of an RNA hairpin loop, in particular when using a vector according to the invention. To afford protection from degradation, it is expedient for the nucleotides to be chemically modified in the loop region between the double-stranded structure.

The chemical linkage is expediently formed by a covalent or ionic bond, a hydrogen bond, hydrophobic interactions, preferably van-der-Waals or stacking interactions, or by metal-ion coordination. In an especially advantageous aspect, it can be formed at least one, preferably both, end(s) of the complementary region II.

It has furthermore proved to be advantageous for the chemical linkage to be formed by one or more linkage groups, the linkage groups preferably being poly(oxyphosphinicooxy-1,3-propanediol) and/or polyethylene glycol chains. The chemical linkage can also be formed by purine analogs used in place of purines in the complementary regions II. It is also advantageous for the chemical linkage to be formed by azabenzene units introduced into the complementary regions II. Moreover, it can be formed by branched nucleotide analogs used in place of nucleotides in the complementary regions II.

It has proved expedient to use at least one of the following groups for generating the chemical linkage: methylene blue; bifunctional groups, preferably bis(2-chloroethyl)amine; N-acetyl-N'-(p-glyoxyl-benzoyl)cystamine; 4-thiouracil; psoralen. The chemical linkage can furthermore be formed by thiophosphoryl groups provided at the ends of the double-stranded region. The chemical linkage at the ends of the double-stranded region is preferably formed by triple-helix bonds.

The chemical linkage can expediently be induced by ultraviolet light.

The nucleotides of the dsRNA can be modified. This counteracts the activation, in the cell, of a double-stranded-RNA-dependent protein kinase, PKR. Advantageously, at least one 2'-hydroxyl group of the nucleotides of the dsRNA in the complementary region II is replaced by a chemical group, preferably a 2'-amino or a 2'-methyl group. At least one nucleotide in at least one strand of the complementary region II can also be a locked nucleotide with a sugar ring which is chemically modified, preferably by a 2'-O, 4'-C methylene bridge. Advantageously, several nucleotides are locked nucleotides.

A further especially advantageous embodiment provides that the dsRNA or the vector is bound to, associated with or surrounded by, at least one viral coat protein which originates from a virus, is derived therefrom or has been prepared synthetically. The coat protein can be derived from polyomavirus. The coat protein can contain the polyomavirus virus protein 1 (VP1) and/or virus protein 2 (VP2). The use of such coat proteins is known from, for example, DE 196 18 797 A1, whose disclosure is herewith incorporated. —The abovementioned features considerably facilitate the introduction of the dsRNA or of the vector into the cell.

When a capsid or capsid-type structure is formed from the coat protein, one side preferably faces the interior of the capsid or capsid-type structure. The construct formed is particularly stable.

The dsRNA can be complementary to the primary or processed RNA transcript of the target gene. —The cell can be a vertebrate cell or a human cell.

At least two dsRNAs which differ from each other or at least one vector encoding them can be introduced into the cell, where at least segments of one strand of each dsRNA are complementary to in each case one of at least two different target genes. This makes it possible simultaneously to inhibit the expression of at least two different target genes. In order to suppress, in the cell, the expression of a double-stranded-RNA-dependent protein kinase, PKR, one of the target genes is advantageously the PKR gene. This allows effective suppression of the PKR activity in the cell.

The invention furthermore provides a medicament with at least one oligoribonucleotide with double-stranded structure (dsRNA) for inhibiting the expression of a given target gene, where one strand of the dsRNA has a region I where at least segments are complementary to the target gene. —Surprisingly, it has emerged that such a dsRNA is suitable as medicament for inhibiting the expression of a given gene in mammalian cells. In comparison with the use of single-stranded oligoribonucleotides, the inhibition is already caused at concentrations which are lower by at least one order of magnitude. The medicament according to the invention is highly effective. Lesser side effects can be expected.

The invention furthermore provides a medicament with at least one vector for coding at least one oligoribonucleotide with double-stranded structure (dsRNA) for inhibiting the expression of a given target gene, where one strand of the dsRNA has a region I where at least segments are complementary to the target gene. —The medicament proposed exhibits the abovementioned advantages. By using a vector, in particular production costs can be reduced.

In a particularly advantageous embodiment, the complementary region I has not more than 49 successive nucleotide pairs. —Surprisingly, it has emerged that an effective inhibition of the expression of the target gene can be achieved even when the complementary region I is not more than 49 base pairs in length. The procedure of providing such oligoribonucleotides is less complicated.

The invention furthermore provides a use of an oligoribonucleotide with double-stranded structure (dsRNA) for preparing a medicament for inhibiting the expression of a given target gene, where one strand of the dsRNA has a region I where at least segments are complementary to the target gene. —Surprisingly, such a dsRNA is suitable for preparing a medicament for inhibiting the expression of a given gene. Compared with the use of single-stranded oligoribonucleotides, the inhibition is already caused at concentrations which are lower by one order of magnitude when using dsRNA. The use according to the invention thus makes possible the preparation of particularly effective medicaments.

The invention furthermore provides the use of a vector for coding at least one oligoribonucleotide with double-stranded structure (dsRNA) for preparing a medicament for inhibiting the expression of a given target gene, where one strand of the dsRNA has a region I where at least segments are complementary to this target gene. —The use of a vector makes possible a particularly effective gene therapy.

With regard to advantageous embodiments of the medicament and of the use, reference is made to the description of the above features.

Figure 2:
Figure 3:
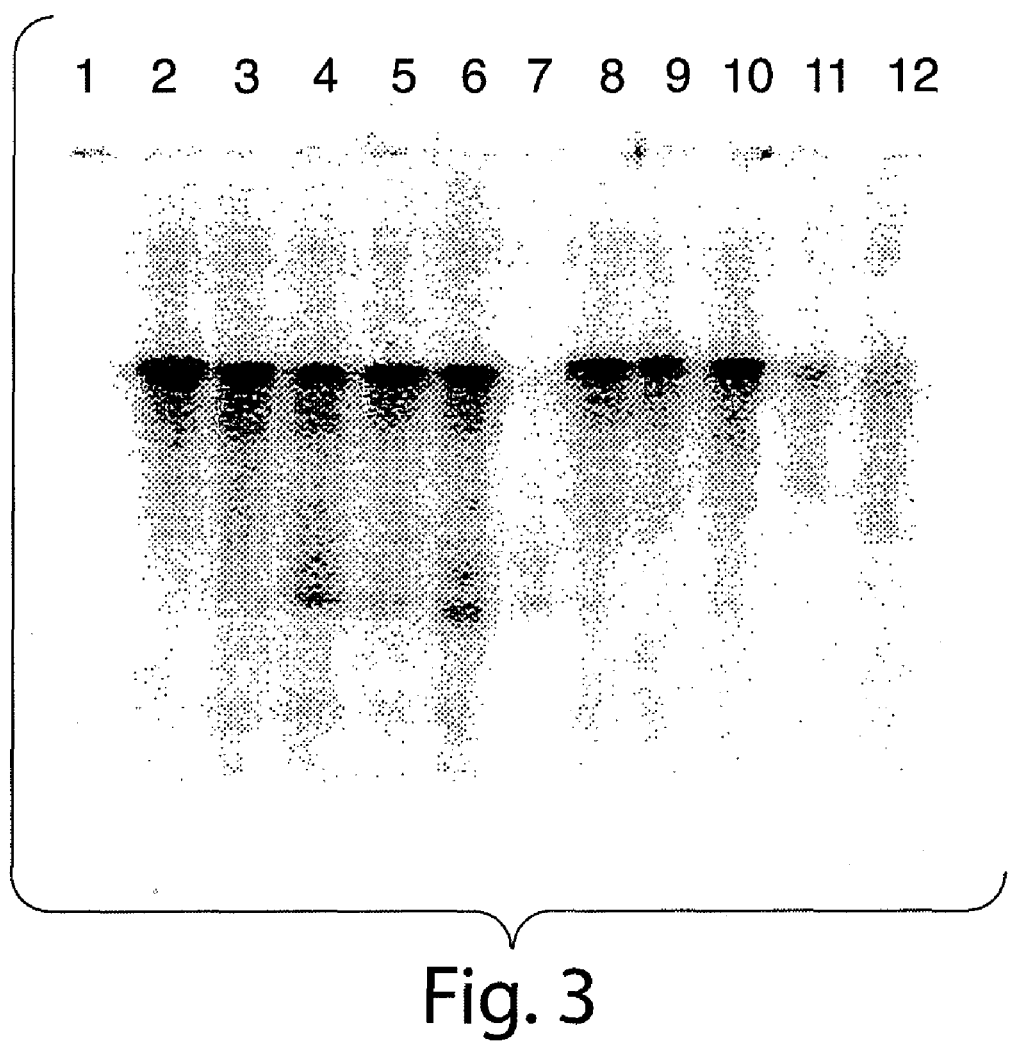

Use examples of the invention are illustrated in greater detail hereinbelow with reference to the figures, in which:

FIG. 1 shows the schematic representation of a plasmid for the in vitro transcription with T7- and SP6-polymerase, FIG. 2 shows RNA following electrophoresis on an 8% polyacrylamide gel and staining with ethidium bromide, FIG. 3 shows a representation of radioactive RNA transcripts following electrophoresis on an 8% polyacrylamide gel with 7 M urea by means of an instant imager, and FIGS. 4a-e show Texas Red and YFP fluorescence in murine fibroblasts.

USE EXAMPLE 1

The inhibition of transcription was detected by means of sequence homologous dsRNA in an in vitro transcription system with a nuclear extract from human HeLa cells. The DNA template for this experiment was plasmid pCMV1200 which had been linearized by means of BamHI.

Generation of the Template Plasmids:

The plasmid shown in FIG. 1 was constructed for use in the enzymatic synthesis of the dsRNA. To this end, a polymerase chain reaction (PCR) with the "positive control DNA" of the HelaScribe® Nuclear Extract in vitro transcription kit by Promega, Madison, USA, as DNA template was first carried out. One of the primers used contained the sequence of an EcoRI cleavage site and of the T7 RNA polymerase promoter as shown in sequence listing No. 1. The other primer contained the sequence of a BamHI cleavage site and of the SP6 RNA polymerase promoter as shown in sequence listing No. 2. In addition, the two primers had, at the 3' ends, regions which were identical with or complementary to the DNA template. The PCR was carried out by means of the "Taq PCR Core Kits" by Qiagen, Hilden, Germany, following the manufacturer's instructions. 1.5 mM $MgCl_2$, in each case 200 µM dNTP, in each case 0.5 µM primer, 2.5 U Taq DNA polymerase and approximately 100 ng of "positive control DNA" were employed as template in PCR buffer in a volume of 100 µl. After initial denaturation of the template DNA by heating for 5 minutes at 94° C., amplification was carried out in 30 cycles of denaturation for in each case 60 seconds at 94° C., annealing for 60 seconds at 5° C. below the calculated melting point of the primers and polymerization for 1.5-2 minutes at 72° C. After a final polymerization of 5 minutes at 72° C., 5 µl of the reaction were analyzed by agarose-gel electrophoresis. The length of the DNA fragment amplified thus was 400 base pairs, 340 base pairs corresponding to the "positive control DNA". The PCR product was purified, hydrolyzed with EcoRI and BamHI and, after repurification, employed in the ligation together with a pUC18 vector which had also been hydrolyzed by EcoRI and BamHI. *E. coli* XL1-blue was then transformed. The plasmid obtained (pCMV5) carries a DNA fragment whose 5' end is flanked by the T7 promoter and whose 3' end is flanked by the SP6 promoter. By linearizing the plasmid with BamHI, it can be employed in vitro with the T7-RNA polymerase for the run-off transcription of a single-stranded RNA which is 340 nucleotides in length and shown in sequence listing No. 3. If the plasmid is linearized with EcoRI, it can be employed for the run-off transcription with SP6 RNA polymerase, giving rise to the complementary strand. In accordance with the method outlined hereinabove, an RNA 23 nucleotides in length was also synthesized. To this end, a DNA shown in sequence listing No. 4 was ligated with the pUC18 vector via the EcoRI and BamHI cleavage sites.

Plasmid pCMV1200 was constructed as DNA template for the in-vitro transcription with HeLa nuclear extract. To this end, a 1 191 bp EcoRI/BamHI fragment of the positive control DNA contained in the HeLaScribe® Nuclear Extract in vitro transcription kit was amplified by means of PCR. The amplified fragment encompasses the 828 bp "immediate early" CMV promoter and a 363 bp transcribable DNA fragment. The PCR product was ligated to the vector pGEM-T via "T-overhang" ligation. A BamHI cleavage site is located at the 5' end of the fragment. The plasmid was linearized by hydrolysis with BamHI and used as template in the run-off transcription.

In-Vitro Transcription of the Complementary Single Strands:

pCMV5 plasmid DNA was linearized with EcoRI or BamHI. It was used as DNA template for an in-vitro transcription of the complementary RNA single strands with SP6 and T7 RNA polymerase, respectively. The "Riboprobe in vitro Transcription" system by Promega, Madison, USA, was employed for this purpose. Following the manufacturer's instructions, 2 µg of linearized plasmid DNA were incubated in 100 µl of transcription buffer and 40 U T7 or SP6 RNA polymerase for 5-6 hours at 37° C. The DNA template was subsequently degraded by addition of 2.5 µl of RNase-free DNase RQ1 and incubation for 30 minutes at 37° C. The transcription reaction was made up to 300 µl with $H_2O$ and purified by phenol extraction. The RNA was precipitated by addition of 150 µl of 7 M ammonium acatate [sic] and 1 125 µl of ethanol and stored at −65° C. until used for the hybridization.

Generation of the RNA Double Strands:

For the hybridization, 500 µl of the single-stranded RNA which had been stored in ethanol and precipitated were spun down. The resulting pellet was dried and taken up in 30 µl of PIPES buffer, pH 6.4 in the presence of 80% formamide, 400 mM NaCl and 1 mM EDTA. In each case 15 µl of the complementary single strands were combined and heated for 10 minutes at 85° C. The reactions were subsequently incubated overnight at 50° C. and cooled to room temperature.

Only approximately equimolar amounts of the two single strands were employed in the hybridization. This is why the dsRNA preparations contained single-stranded RNA (ssRNA) as contaminant. In order to remove these ssRNA contaminants, the reactions were treated, after hybridization, with the single-strand-specific ribonucleases bovine pancreatic RNase A and *Aspergillus oxyzae* RNase T1. RNase A is an endoribonuclease which is specific for pyrimidines. RNase T1 is an endoribonuclease which preferentially cleaves at the 3' side of guanosines. dsRNA is no substrate for these ribonucleases. For the RNase treatment, the reactions in 300 µl of Tris, pH 7.4, 300 mM NaCl and 5 mM EDTA were treated with 1.2 µl of RNaseA at a concentration of 10 mg/ml and 2 µl of RNaseT1 at a concentration of 290 µg/ml. The reactions were incubated for 1.5 hours at 30° C. Thereupon, the RNases were denatured by addition of 5 µl of proteinase K at a concentration of 20 mg/ml and 10 µl of 20% SDS and incubation for 30 minutes at 37° C. The dsRNA was purified by phenol extraction and precipitated with ethanol. To verify the completeness of the RNase digestion, two control reactions were treated with ssRNA analogously to the hybridization reactions.

The dried pellet was taken up in 15 µl of TE buffer, pH 6.5, and subjected to native polyacrylamide gel electrophoresis on an 8% gel. The acrylamide gel was subsequently stained in an ethidium bromide solution and washed in a water bath. FIG. 2 shows the RNA which had been visualized in a UV transilluminator. The sense RNA which had been applied to lane 1 and the antisense RNA which had been applied to lane 2 showed a different migration behavior under the chosen conditions than the dsRNA of the hybridization reaction which had been applied to lane 3. The RNase-treated sense RNA and antisense RNA which had been applied to lanes 4 and 5, respectively, produced no visible band. This shows that the single-stranded RNAs had been degraded completely. The RNase-treated dsRNA of the hybridization reaction which had been applied to lane 6 is resistant to RNase treatment. The band which migrates faster in the native gel in comparison with the dsRNA applied to lane 3 results from dsRNA which is free from ssRNA. In addition to the dominant main band, weaker bands which migrate faster are observed after the RNase treatment.

In-Vitro Transcription Test with Human Nuclear Extract:

Using the HeLaScribe® Nuclear Extract in vitro transcription kit by Promega, Madison, USA, the transcription efficiency of the abovementioned DNA fragment which is present in plasmid pCMV1200 and homologous to the "positive control DNA" was determined in the presence of the dsRNA (dsRNA-CMV5) with sequence homology. Also, the effect of the dsRNA without sequence homology, which corresponds to the yellow fluorescent protein (YFP) gene (dsRNA-YRP), was studied. This dsRNA had been generated analogously to the dsRNA with sequence homology. The sequence of a strand of this dsRNA can be found in sequence listing No. 5. Plasmid pCMV1200 was used as template for the run-off transcription. It carries the "immediate early" cytomegalovirus promoter which is recognized by the eukaryotic RNA polymerase II, and a transcribable DNA fragment. Transcription was carried out by means of the HeLa nuclear extract, which contains all the proteins which are necessary for transcription. By addition of [•-$^{32}$P]rGTP to the transcription reaction, radiolabeled transcript was obtained. The [•-$^{32}$P]rGTP used had a specific activity of 400 Ci/mmol, 10 mCi/ml. 3 mM MgCl$_2$, in each case 400 µM rATP, rCTP, rUTP, 16 µM rGTP, 0.4 µM [•-$^{32}$P]rGTP and depending on the experiment 1 fmol of linearized plasmid DNA and various amounts of dsRNA in transcription buffer were employed per reaction. Each batch was made up to a volume of 8.5 µl with H$_2$O. The reactions were mixed carefully. To start the transcription, 4 U HeLa nuclear extract in a volume of 4 µl were added and incubated for 60 minutes at 30° C. The reaction was stopped by addition of 87.5 µl of quench mix which had been warmed to 30° C. To remove the proteins, the reactions were treated with 100 µl of phenol/chloroform/isoamyl alcohol (25:24:1 v/v/v) saturated with TE buffer, pH 5.0, and the reactions were mixed vigorously for 1 minute. For phase separation, the reactions were spun for approximately 1 minute at 12 000 rpm and the top phase was transferred into a fresh reaction vessel. Each reaction was treated with 250 µl of ethanol. The reactions were mixed thoroughly and incubated for at least 15 minutes on dry ice/methanol. To precipitate the RNA, the reactions were spun for 20 minutes at 12 000 rpm and 40° C. The supernatant was discarded. The pellet was dried in vacuo for 15 minutes and resuspended in 10 µl of H$_2$O. Each reaction was treated with 10 µl of denaturing loading buffer. The free GTP was separated from the transcript formed by means of denaturing polyacrylamide gel electrophoresis on an 8% gel with 7 M urea. The RNA transcripts formed upon transcription with HeLa nuclear extract, in denaturing loading buffer, were heated for 10 minutes at 90° C. and 10 µl aliquots were applied immediately to the freshly washed pockets. The electrophoresis was run at 40 mA. The amount of the radioactive ssRNA formed upon transcription was analyzed after electrophoresis with the aid of an Instant Imager.

FIG. 3 shows the radioactive RNA from a representative test, shown by means of the Instant Imager. Samples obtained from the following transcription reactions were applied:
Lane 1: without template DNA, without dsRNA;
Lane 1: 50 ng of template DNA, without dsRNA;
Lane 3: 50 ng of template DNA, 0.5 µg of dsRNA YFP;
Lane 4: 50 ng of template DNA, 1.5 µg of dsRNA YFP;
Lane 5: 50 ng of template DNA, 3 µg of dsRNA YFP;
Lane 6: 50 ng of template DNA, 5 µg of dsRNA YFP;
Lane 7: without template DNA, 1.5 dsRNA YFP;
Lane 8; 50 ng of template DNA, without dsRNA;
Lane 9: 50 ng of template DNA, 0.5 µg of dsRNA CMV5;
Lane 10: 50 ng of template DNA, 1.5 µg of dsRNA CMV5;
Lane 11: 50 ng of template DNA, 3 µg of dsRNA CMV5;
Lane 12: 50 ng of template DNA, 5 µg of dsRNA CMV5;

It emerged that the amount of transcript was reduced markedly in the presence of dsRNA with sequence homology in comparison with the control reaction without dsRNA and with the reactions with dsRNA YFP without sequence homology. The positive control in lane 2 shows that radioactive transcript was formed upon the in-vitro transcription with HeLa nuclear extract. The reaction is used for comparison with the transcription reactions which had been incubated in the presence of dsRNA. Lanes 3 to 6 show that the addition of non-sequentially-specific dsRNA YFP had no effect on the amount of transcript formed. Lanes 9 to 12 show that the addition of an amount of between 1.5 and 3 µg of sequentially-specific dsRNA CMV5 leads to a reduction in the amount of transcript formed. In order to exclude that the effects observed are based not on the dsRNA but on any contamination which might have been carried along accidentally during the preparation of the dsRNA, a further control was carried out. Single-stranded RNA was transcribed as described above and subsequently subjected to the RNase treatment. It was demonstrated by means of native polyacrylamide gel electrophoresis that the ssRNA had been degraded completely. This reaction was subjected to phenol extraction and ethanol precipitation and subsequently taken up in PE buffer, as were the hybridization reactions. This gave a sample which contained no RNA but had been treated with the same enzymes and buffers as the dsRNA. Lane 8 shows that the addition of this sample had no effect on transcription. The reduction of the transcript upon addition of sequence-specific dsRNA can therefore be ascribed unequivocally to the dsRNA itself. The reduction of the amount of transcript of a gene in the presence of dsRNA in a human transcription system indicates an inhibition of the expression of the gene in question. This effect can be attributed to a novel mechanism caused by the dsRNA.

USE EXAMPLE 2

The test system used for these in-vivo experiments was the murine fibroblast cell line NIH3T3, ATCC CRL-1658. The YFP gene was introduced into the nuclei with the aid of microinjection. Expression of YFP was studied under the effect of simultaneously cotransfected dsRNA with sequence homology. This dsRNA YFP shows homology with the 5'-region of the YFP gene over a length of 315 bp. The nucleotide sequence of a strand of the dsRNA YRP is shown in sequence listing No. 5. Evaluation under the fluorescence microscope was carried out 3 hours after injection with reference to the greenish-yellow fluorescence of the YFP formed.

Construction of the Template Plasmid, and Preparation of the dsRNA:

A plasmid was constructed following the same principle as described in use example 1 to act as template for the production of the YFP dsRNA by means of T7 and SP6 in-vitro transcription. Using the primer Eco_T7_YFP as shown in sequence listing No. 6 and Bam_SP6_YFP as shown in sequence listing No. 7, the desired gene fragment was amplified by PCR and used analogously to the above description for preparing the dsRNA. The dsRNA YFP obtained is identical to the dsRNA used in use example 1 as non-sequence-specific control.

A dsRNA linked chemically at the 3' end of the RNA as shown in sequence listing No. 8 to the 5' end of the complementary RNA via a C18 linker group was prepared (L-dsRNA). To this end, synthons modified by disulfide bridges were used. The 3'-terminal synthon is bound to the solid support via the 3' carbon with an aliphatic linker group via a disulfide bridge. In the 5'-terminal synthon of the complementary oligoribonucleotide which is complementary to the 3'-terminal synthon of the one oligoribonucleotide, the 5'-trityl protecting group is bound via a further aliphatic linker and a disulfide bridge. Following synthesis of the two single strands, removal of the protecting groups and hybridization of the complementary oligoribonucleotides, the thiol groups which form are brought into spatial vicinity. The single strands are linked to each other by, oxidation via their aliphatic linkers and a disulfide bridge. This is followed by purification with the aid of HPLC.

Preparation of the Cell Cultures:

The cells were incubated in DMEM supplemented with 4.5 g/l glucose, 10% fetal bovine serum in culture dishes at 37° C. under a 7.5% $CO_2$ atmosphere and passaged before reaching confluence. The cells were detached with trypsin/EDTA. To prepare for microinjection, the cells were transferred into Petri dishes and incubated further until microcolonies formed.

Microinjection:

For the microinjection, the culture dishes were removed from the incubator for approximately 10 minutes. Approximately 50 nuclei were injected singly per reaction within a marked area using the AIS microinjection system from Carl Zeiss, Göttingen, Germany. The cells were subsequently incubated for three more hours. For the microinjection, borosilicate glass capillaries from Hilgenberg GmbH, Malsfeld, Germany, with a diameter of less than 0.5 µm at the tip were prepared. The microinjection was carried out using a micromanipulator from Narishige Scientific Instrument Lab., Tokyo, Japan. The injection time was 0.8 seconds and the pressure was approximately 100 hPa. The transfection was carried out using the plasmid pCDNA YFP, which contains an approximately 800 bp BamHI/EcoRI fragment with the YFP gene in vector pcDNA3. The samples injected into the nuclei contained 0.01 µg/µl of pCDNA-YFP and Texas Red coupled to dextran-70000 in 14 mM NaCl, 3 mM KCl, 10 nM $KPO_4$ [sic], ph 7.5. Approximately 100 pl of RNA with a concentration of 1 µM or, in the case of the L-dsRNA, 375 µM were additionally added.

The cells were studied under a fluorescence microscope with excitation with the light of the excitation wavelength of Texas Red, 568 nm, or of YFP, 488 nm. Individual cells were documented by means of a digital camers. FIGS. 4a-e show the result for NIH3T3 cells. In the cells shown in FIG. 4a, sense-YFP-ssRNA has been injected, in FIG. 4b antisense-YFP-ssRNA, in FIG. 4c dsRNA-YFP, in FIG. 4d no RNA and in FIG. 4e L-dsRNA.

The field on the left shows in each case the fluorescence of cells with excitation at 568 nm. The fluorescence of the same cells at an excitation of 488 nm is seen on the right. The Texas Red fluorescence of all the cells shown demonstrates that the injection solution had been applied successfully into the nuclei and that cells with successful hits were still alive after three hours. Dead cells no longer showed. Texas Red fluorescence.

Figure 4A:
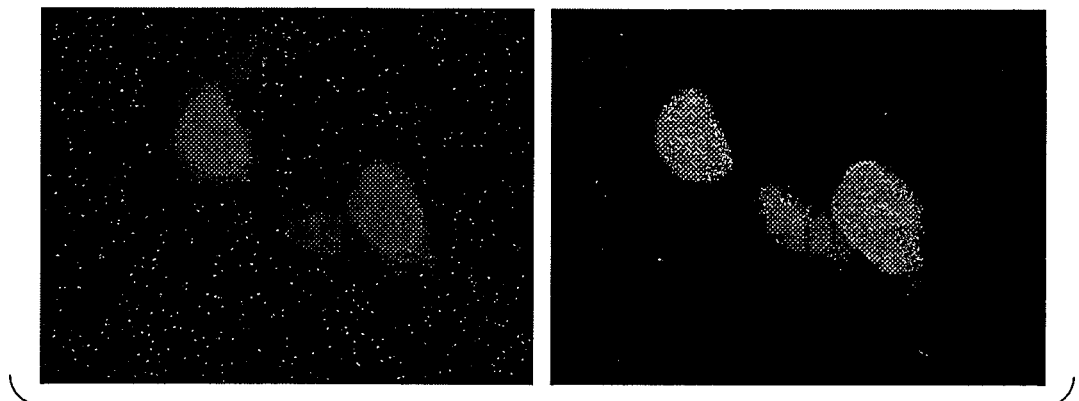
Figure 4B:
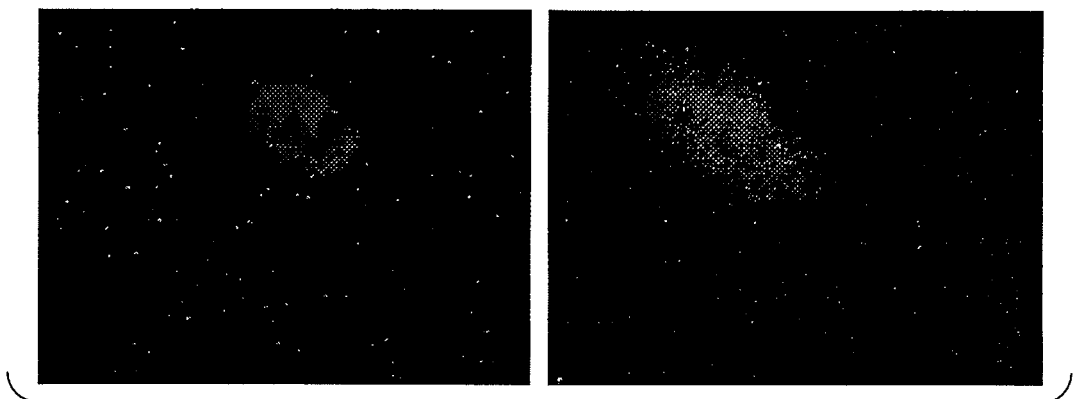
Figure 4C:
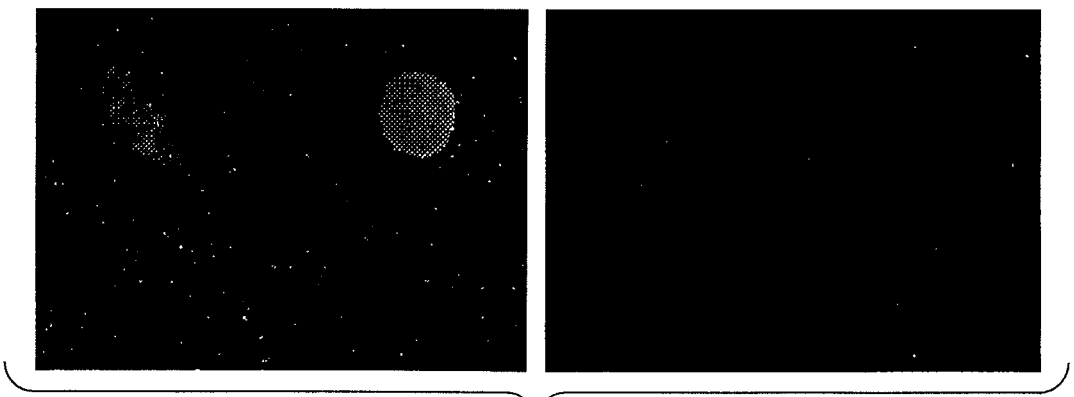
Figure 4D:
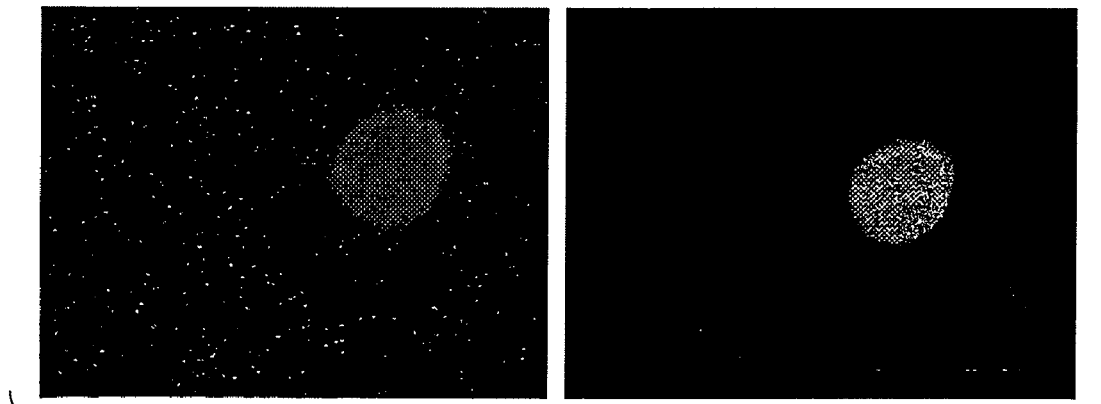
Figure 4E:
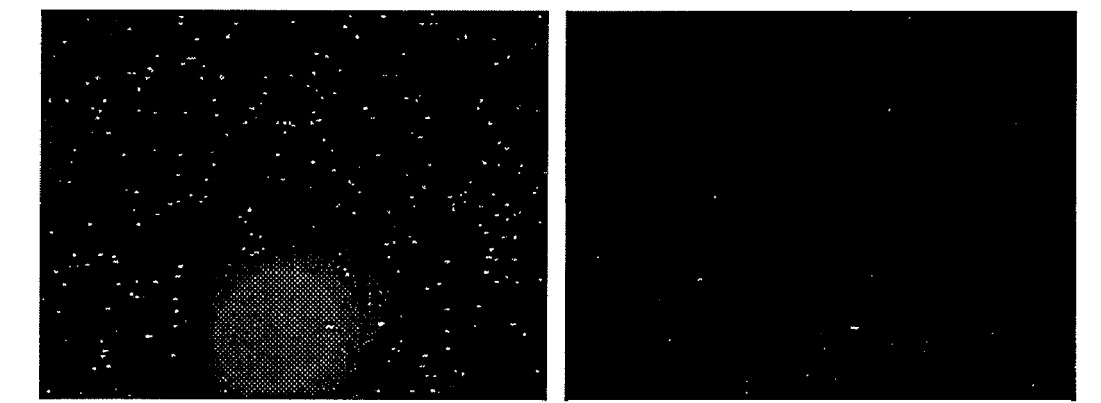

The right fields of each of FIGS. 4a and 4b show that YFP expression was not visibly inhibited when the single-stranded RNA was injected into the nuclei. The right field of FIG. 4c shows cells whose YFP fluorescence was no longer detectable after the injection of dsRNA-YFP. FIG. 4d shows cells into which no RNA had been injected, as control. The cell shown in FIG. 4e shows YFP fluorescence which can no longer be detected owing to the injection of the L-dsRNA which shows regions with sequence homology to the YFP gene. This result demonstrates that even shorter dsRNAs can be used for specifically inhibiting gene expression in mammals when the double strands are stabilized by chemically linking the single strands.

LITERATUR

Asanuma, H., Ito, T., Yoshida, T., Liang, X. & Komiyama, M. (1999). Photoregulation der Bildung und Dissoziation eines DNA-Duplexes durch cis-trans-Isomerisierung einer Azobenzoleinheit. *Angew. Chem.* 111, 2547-2549.

Azhayeva, E., Azhayev, A., Auriola, S., Tengvall, U., Urtti, A. & Lönnberg, H. (1997). Inhibitory properties of double helix forming circular oligonucleotides. *Nucl. Acids Res.* 25, 4954-4961.

Castelli, J., Wood, K. A. & Youle, R. J. (1998). The 2-5A system in viral infection and apoptosis. *Biomed. Pharmacother.* 52, 386-390.

Dolinnaya, N. G., Blumenfeld, M., Merenkova, I., Oretskaya, T. S., Krynetskaya, N. F., Ivanovskaya, M. G., Vasseur, M. & Shabarova, Z. A. (1993). Oligonucleotide circularization by template-directed chemical ligation. *Nucl. Acids Res.* 21, 5403-5407.

Expert-Bezancon, A., Milet, M. & Carbon, P. (1983). Precise localization of several covalent RNA-RNA cross-link in *Escherichia coli* 16S RNA. *Eur. J. Biochem.* 136, 267-274.

Fire, A., Xu, S., Mongomery, M. K., Kostas, S. A., Driver, S. E. & Mello, C. C. (1998). Potent and specific geneticinterference by double-stranded RNA in *Caenorhabditis elegans*. *Nature* 391, 806-811.

Gao, H., Yang, M., Patel, R. & Cook, A. F. (1995). Circulaization of oligonucleotides by disulfide bridge formation. *Nucl. Acids Res.* 23, 2025-2029.

Gryaznov, S. M. & Letsinger, R. L. (1993). Template controlled coupling and recombination of oligonucleotide blocks containing thiophosphoryl groups. *Nucl Acids Res.* 21, 1403-1408.

Kaufman, R. J. (1999). Double-stranded RNA-activated protein kinase mediates virus-induced apoptosis: A new role for an old actor. *Proc. Natl. Acad. Sci. USA* 96, 11693-11695.

Lipson, S. E. & Hearst, J. E. (1988). Psoralen cross-linking of ribosomal RNA. In *Methods in Enzymology* Anonymous pp. 330-341.

Liu, Z. R., Sargueil, B. & Smith, C. W. (1998). Detection of a novel ATP-dependent cross-linked protein at the 5' splice site-U1 small nuclear RNA duplex by methylene blue-mediated photo-cross-linking. *Mol. Cell. Biol.* 18, 6910-6920.

Micura, R. (1999). Cyclic oligoribonucleotides (RNA) by solid-phase synthesis. *Chem. Eur. J.* 5, 2077-2082.

Skripkin, E., Isel, C., Marquet, R., Ehresmann, B. & Ehresmann, C. (1996). Prsoralen crosslinking between human immunodeficiency virus type 1 RNA and primer tRNA$_3^{Lys}$. *Nucl. Acids Res.* 24, 509-514.

Wang, S. & Kool, E. T. (1994). Circular RNA oligonucleotides. Synthesis, nucleic acid binding properties, and a comparison with circular DNAs. *Nucl. Acids Res.* 22, 2326-2333.

Wang, Z. & Rana, T. M. (1996). RNA conformation in the Tat-TAR complex determined by site-specific photo-cross-linking. *Biochem.* 35, 6491-6499.

Watkins, K. P. & Agabian, N. (1991). In vivo UV cross-linking of U snRNAs that participate in trypanosome trans-plicing. *Genes & Development* 5, 1859-1869.

Wengel, J. (1999). Synthesis of 3'-C- and 4'-C-branched oligodeoxynucleotides and the development of locked nucleic acid (LNA). *Acc. Chem. Res.* 32, 301-310.

Zwieb, C., Ross, A., Rinke, J., Meinke, M. & Brimacombe, R. (1978). Evidence for RNA-RNA cross-link formation in *Escherichia coli* ribosomes. *Nucl. Acids Res.* 5, 2705-2720.

---

The invention claimed is:

1. A double stranded RNA (dsRNA) packaged in a liposome,
wherein said dsRNA consists of two separate complementary oligoribonucleotide strands comprising a first strand and a second strand that are linked by a linker,
wherein each of said strands consists of 21 nucleotides in length,
wherein one strand of said strands of said dsRNA is complementary to less than the full length of a third strand, said third strand comprising an RNA transcript of a mammalian target gene, and
wherein an amount of said third strand is capable of being reduced in response to said dsRNA being introduced into the presence of said third strand in a mammalian cell, thereby being capable of specifically inhibiting the expression of said mammalian target gene.

2. The dsRNA of claim 1, wherein said separate oligoribonucleotide strands are chemically linked to reduce dissociation as compared to non-linked oligoribonucleotide strands.

3. The dsRNA of claim 2, wherein said chemical linkage is formed by a covalent bond or hydrogen bound.

4. The dsRNA of claim 1, wherein at least one of said oligoribonucleotide strands comprises at least one chemically modified nucleotide.

5. The dsRNA of claim 4, wherein said chemically modified nucleotide is a 2'-modified nucleotide.

6. The dsRNA of claim 5, wherein said 2'- modified nucleotide is a 2'-methyl substituted nucleotide.

7. The dsRNA of claim 5, wherein said 2'- modified nucleotide is a 2'-amino substituted nucleotide.

8. The dsRNA of claim 4, wherein said chemically modified nucleotide is a locked nucleotide.

9. The dsRNA of claim 1, wherein said dsRNA is modified so as to be resistant to RNA degradation.

10. The dsRNA of claim 1, wherein said two separate complementary strands are fully complementary to each other.

11. The dsRNA of claim 1, wherein said dsRNA is capable of specifically inhibiting the expression of said target gene using dsRNA-mediated interference.

12. The dsRNA of claim 1, wherein the linker comprises a covalent linker.

13. The dsRNA of claim 12, wherein the covalent linker comprises a C18 linker.

14. The dsRNA of claim 1, wherein the linker comprises a labile linker.

15. The dsRNA of claim 14, wherein the labile linker comprises a disulfide bridge.

16. The dsRNA of claim 1, wherein the linker is a covalent linker that links a 3' end of one of the two strands to a 5' end of another of the two strands.

17. The dsRNA of claim 16, wherein the covalent linker is a C18 linker.

18. The dsRNA of claim 4, wherein only one nucleotide of at least one of said oligoribonucleotide strands is a chemically modified nucleotide.

19. The dsRNA of claim 1, wherein one of the strands of said dsRNA is capable of hybridizing to the RNA transcript to specifically inhibit expression of the target gene.

20. The dsRNA of claim 1, wherein said second and third strands are sense strands and wherein said first strand is an antisense strand.

21. The dsRNA of claim 1, wherein said first strand is capable of hybridizing to said third strand to reduce the amount of said third strand.

22. The dsRNA of claim 1, wherein a 3' end of one of said first and second strands is linked to a 5' end of another of said first and second strands with a carbon-carbon linker.

* * * * *

UNITED STATES PATENT AND TRADEMARK OFFICE
CERTIFICATE OF CORRECTION

| | | |
|---|---|---|
| PATENT NO. | : 8,114,981 B2 | Page 1 of 1 |
| APPLICATION NO. | : 11/982441 | |
| DATED | : February 14, 2012 | |
| INVENTOR(S) | : Kreutzer et al. | |

It is certified that error appears in the above-identified patent and that said Letters Patent is hereby corrected as shown below:

Column 15, line 22, Claim 3, after "hydrogen" please change "bound" to "bond."

Signed and Sealed this
Twenty-fourth Day of April, 2012

David J. Kappos
*Director of the United States Patent and Trademark Office*

SEQUENCE LISTING

```
<160> NUMBER OF SEQ ID NOS: 8

<210> SEQ ID NO 1
<211> LENGTH: 45
<212> TYPE: DNA
<213> ORGANISM: Artificial Sequence
<220> FEATURE:
<223> OTHER INFORMATION: Description of the artificial sequence:
      EcoRI cleavage site, T7 RNA Polymerase promoter

<400> SEQUENCE: 1
ggaattctaa tacgactcac tatagggcga tcagatctct agaag              45

<210> SEQ ID NO 2
<211> LENGTH: 50
<212> TYPE: DNA
<213> ORGANISM: Artificial Sequence
<220> FEATURE:
<223> OTHER INFORMATION: Description of the artificial sequence:
      BamHI cleavage site, SP6 RNA Polymerase promoter

<400> SEQUENCE: 2
gggatccatt taggtgacac tatagaatac ccatgatcgc gtagtcgata         50

<210> SEQ ID NO 3
<211> LENGTH: 340
<212> TYPE: RNA
<213> ORGANISM: Artificial Sequence
<220> FEATURE:
<223> OTHER INFORMATION: Description of the artificial sequence:
      RNA which corresponds to a sequence from the positive control
      DNA of the HeLa Nuclear Extract in vitro transcription kit from
      Promega

<400> SEQUENCE: 3
ucagaucucu agaagcuuua augcgguagu uuaucacagu uaaauugcua acgcagucag    60
gcaccgugua ugaaaucuaa caaugcgcuc aucgucaucc ucggcaccgu cacccuggau   120
gcuguaggca uaggcuuggu uaugccggua cugccgggcc ucuugcggga uaucguccau   180
uccgacagca ucgccaguca cuauggcgug cugcuagcgc uauaugcguu gaugcaauuu   240
cuaugcgcac ccguucucgg agcacuqucc gaccgcuuug gccgccgccc aguccugcuc   300
gcuucgcuac uuggagccac uaucgacuac gcgaucaugg                        340

<210> SEQ ID NO 4
<211> LENGTH: 363
<212> TYPE: DNA
<213> ORGANISM: Artificial Sequence
<220> FEATURE:
<223> OTHER INFORMATION: Description of the artificial sequence:
      DNA which corresponds to a sequence from the positive control
      DNA of the HeLa Nuclear Extract in vitro transcription kit from
      Promega
```

```
<400> SEQUENCE: 4
tcagatctct agaagcttta atgcggtagt ttatcacagt taaattgcta acgcagtcag    60
gcaccgtgta tgaaatctaa caatgcgctc atcgtcatcc tcggcaccgt caccctggat   120
gctgtaggca taggcttggt tatgccgta ctgccgggcc tcttgcggga tatcgtccat    180
tccgacagca tcgccagtca ctatggcgtg ctgctagcgc tatatgcgtt gatgcaattt   240
ctatgcgcac ccgttctcgg agcactgtcc gaccgctttg gccgccgccc agtcctgctc   300
gcttcgctac ttggagccac tatcgactac gcgatcatgg cgaccacacc cgtcctgtgg   360
atc                                                                 363

<210> SEQ ID NO 5
<211> LENGTH: 315
<212> TYPE: RNA
<213> ORGANISM: Artificial Sequence
<220> FEATURE:
<223> OTHER INFORMATION: Description of the artificial sequence:
      Sequence from the YFP gene

<400> SEQUENCE: 5
auggugagca agggcgagga gcuguucacc ggggugguge ccauccuggu cgagcuggac    60
ggcgacguaa acggccacaa guucagcgug uccggcgagg gcgagggcga ugccaccuac   120
ggcaagcuga cccugaaguu caucugcacc accggcaagc ugcccgugcc cuggcccacc   180
cucgugacca cccugaccua cggcgugcag ugcuucagcc gcuaccccga ccacaugaag   240
cagcacgacu ucuucaaguc cgccaugccc gaaggcuacg uccaggagcg caccaucuuc   300
uucaaggacg acggc                                                    315

<210> SEQ ID NO 6
<211> LENGTH: 52
<212> TYPE: DNA
<213> ORGANISM: Artificial Sequence
<220> FEATURE:
<223> OTHER INFORMATION: Description of the artificial sequence:
      EcoRI cleavage site, T7 RNA Polymerase promoter, complementary
      region to the YFP gene

<400> SEQUENCE: 6
ggaattctaa tacgactcac tatagggcga atggtgagca agggcgagga gc            52

<210> SEQ ID NO 7
<211> LENGTH: 53
<212> TYPE: DNA
<213> ORGANISM: Artificial Sequence
<220> FEATURE:
<223> OTHER INFORMATION: Description of the artificial sequence:
      BamHI cleavage site, SP6 RNA Polymerase promoter, complementary
      region to the YFP gene

<400> SEQUENCE: 7
gggatccatt taggtgacac tatagaatac gccgtcgtcc ttgaagaaga tgg            53

<210> SEQ ID NO 8
<211> LENGTH: 21
<212> TYPE: RNA
<213> ORGANISM: Artificial Sequence
<220> FEATURE:
<223> OTHER INFORMATION: Description of the artificial sequence:
      RNA which corresponds to a sequence from the YFP gene

<400> SEQUENCE: 8
ucgagcugga cggcgacgua a                                              21
```